United States Patent [19]

Kurono et al.

[11] Patent Number: 5,001,240

[45] Date of Patent: Mar. 19, 1991

[54] PROCESS FOR PREPARING OPTICALLY ACTIVE HYDANTOINS

[75] Inventors: Masayasu Kurono, Mie; Yasuaki Kondo, Kasugai; Takuji Yamaguchi, Kuwana; Kenji Miura, Kasugai; Toshinao Usui, Gifu; Naofumi Terada; Kyoichi Asano, both of Nagoya; Kuniharu Mizuno, Aichi; Akira Matsubara, Owari-asahi; Noriaki Kato, Kasugai; Kiichi Sawai, Funabashi, all of Japan

[73] Assignee: Sanwa Kagaku Kenkyyusho Co., Ltd., Aichi, Japan

[21] Appl. No.: 507,608

[22] Filed: Apr. 12, 1990

Related U.S. Application Data

[63] Continuation-in-part of Ser. No. 355,622, May 23, 1989, abandoned, which is a continuation of Ser. No. 90,729, Aug. 28, 1987, Pat. No. 4,861,792.

[30] Foreign Application Priority Data

Aug. 28, 1986 [JP] Japan ................... 61-199924
Nov. 14, 1986 [JP] Japan ................... 61-272612
Apr. 8, 1987 [JP] Japan ................... 62-84577

[51] Int. Cl.⁵ .......................... C07D 405/02
[52] U.S. Cl. ................................ 548/309
[58] Field of Search ........................ 548/309

[56] References Cited

U.S. PATENT DOCUMENTS 4,740,517 4/1988 Kurono et al. ................ 514/389

OTHER PUBLICATIONS

March, J., Advanced Organic Chemistry, 2nd Ed., McGraw Hill, New York, 1977, pp. 106–107, 720 and 726.
The Vocabulary of Organic Chemistry, Milton Orchin et al, p. 187, 1980.

Primary Examiner—Mary C. Lee
Assistant Examiner—Joseph K. McKane
Attorney, Agent, or Firm—Armstrong, Nikaido, Marmelstein, Kubovcik & Murray

[57] ABSTRACT

Hydantoin derivatives and salts thereof, intermediates therefor, process for the preparation thereof, and medicines containing the derivatives, wherein said derivatives have the formula

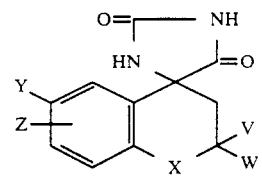

wherein
one of V and W is hydrogen and the other is a halogenomethyl group, 1H-tetrazol-5-yl radical, —COOR group,
in which R is hydrogen atom, an alkyl group, —(CH$_2$CH$_2$O)nCH$_3$ group (n is an integer of 1 to 113) or substituted phenyl,

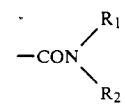

group,
in which $R_1$ and $R_2$ are same or different independently, each is hydrogen atom, an alkyl group, substituted phenyl or —(CH$_2$CH$_2$O)nCH$_3$ group (n has the meaning as referred to) or $R_1$ may form a heterocyclic ring together with $R_2$ and nitrogen or oxygen atom, —CH$_2$OR$_3$ group or

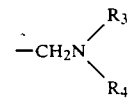

group,
in which $R_3$ and $R_4$ are same or different independently and each is hydrogen atom or an alkyl group,
X is oxygen or sulfur atom, and Y and Z are same or different independently and each is hydrogen atom, a halogen atom, alkyl group, alkoxy group, alkylmercapto group, nitro radical or —NHR$_5$ group, in which R$_5$ is hydrogen atom or an acyl group.

The derivatives and salts thereof are useful for the treatment of complications of diabetes.

3 Claims, No Drawings

PROCESS FOR PREPARING OPTICALLY ACTIVE HYDANTOINS

This application is a continuation-in-part of application Ser. No. 355,622 filed May 23, 1989, now abandoned, which is a continuation of application Ser. No. 090,729 filed Aug. 28, 1987, now U.S. Pat. No. 4,861,792.

BACKGROUND OF THE INVENTION

1. Field of the Invention

The present invention relates to nobel hydantoin derivatives, salts thereof, intermediates therefor and having an optical activity, a process for the preparation of same, and medicines containing the derivative or salt as an effective ingredient to treat complications of diabetes.

The hydantoin derivatives and intermediates are shown by following formula.

Hydantoin derivatives

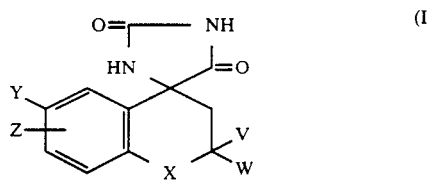

wherein
one of V and W is hydrogen and the other is a halogenomethyl group, 1H-tetrazol-5-yl radical, —COOR group,
in which R is hydrogen atom, an alkyl group, —(CH$_2$CH$_2$O)nCH$_3$ group (n is an integer of 1 to 113) or substituted phenyl,

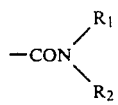

group,
in which R$_1$ and R$_2$ are same or different independently, each is hydrogen atom, an alkyl group, substituted phenyl or —(CH$_2$CH$_2$O)nCH$_3$ group (n has the meaning as referred to) or R$_1$ may form a heterocyclic ring together with R$_2$ and nitrogen or oxygen atom, —CH$_2$OR$_3$ group or

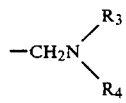

group,
in which R$_3$ and R$_4$ are same or different independently and each is hydrogen atom or an alkyl group,
X is oxygen or sulfur atom, and Y and Z are same or different independently and each is hydrogen atom, a halogen atom, alkyl group, alkoxy group, alkylmercapto group, nitro radical or —NHR$_5$, in which R$_5$ is hydrogen atom or an acyl group.

Intermediates

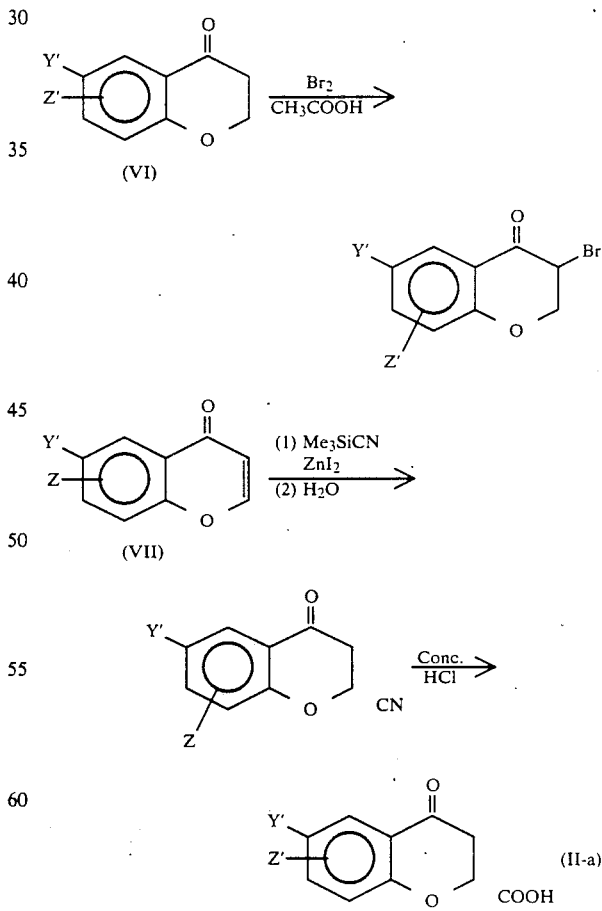

wherein Y' and Z' are same or different independently, each is hydrogen atom, a halogen atom or alkyl group.

2. Related Arts

Racemic 3,4-dihydro-4-oxo-2H-1-benzopyran-2-carboxylic acid derivatives having the chemical formula same with that for the intermediates have been known [Jap. Unexamined Pat. Appln. Gazette No. 200991/1986, "J. Med. Chem." Vol. 14, No. 8, pages 758–766 (1971) and "Liebigs Ann. Chem." pages 1552–1556 (1978)].

According to the process disclosed in said Japanese official gazette, the racemic derivatives (II-a) are prepared as shown in following reaction formula, by brominating 4-chromanone derivative (VI), treating with triethylamine to remove hydrogen bromide and to form a 4-chromenone derivative (VII), treating the derivative with trimethylsilylcyanide to give cyano compound, and treating with concentrated hydrochroric acid to cause hydrolysis of the cyanide.

wherein Y' and Z' are same or different independently and each is hydrogen atom, a halogen atom or alkyl group.

However, this process can not always be said as preferable one, since it requires the expensive reagent of trimethylsilylcyanide.

According to the process described in said J. Med. Chem., the racemic derivatives (II-b) are prepared as shown in the following reaction formula, by condensationally reacting 4-chlorophenol with α-bromo-γ-butylolactone to form the compound (VIII), oxidationally opening the ring with chromium trioxide to form the dicarboxylic acid (IX), and then treating with concentrated surfuric acid to cause a ring closure.

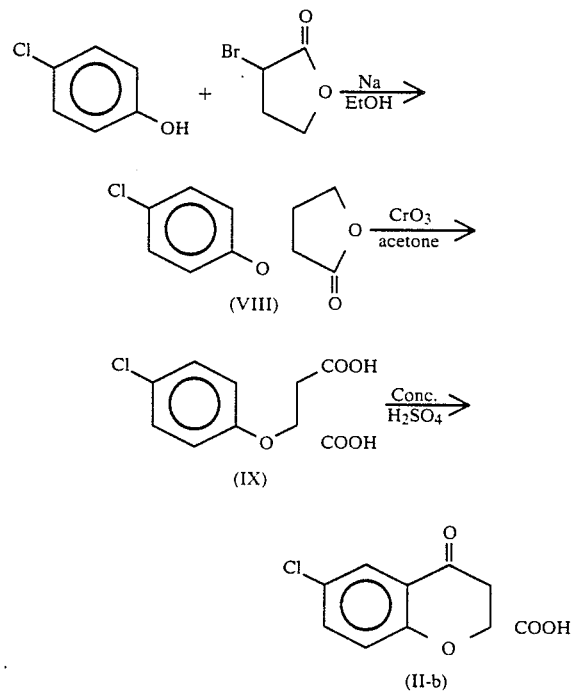

This process has also the disadvantage of that yield of the product is not so high of about 55 to 66%.

According to the process described in said Liebigs Ann. Chem., the racemic derivatives (II-c) are prepared as shown in the following reaction formula, by subjecting the monophenyl ester (X) of furmaric acid to Fries rearrangement, in the presence of aluminum chloride, and then causing a ring closure in sodium carbonate solution.

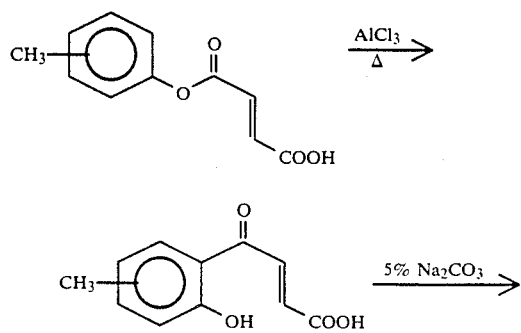

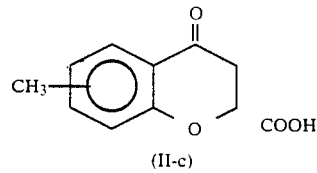

This process has disadvantages of that the synthetic yield of the raw material and yield of the Fries rearrangement reaction are low of about 30 to 52% and 16 to 50%, respectively.

Further, please note that each of the products obtained by such conventional processes has no optical activity and thus should be made into an optical active one, when the product is to be employed as the raw material to synthesize the hydantoin derivatives which are useful as the effective ingredient for medicines to prevent or cure the complications of diabetes.

Turning now to the diabetes, various studies have been made to seek compounds as effective ingredient for the medicine to prevent or cure the diabetes, which medicine can be administered in oral rout. As a result, various compounds of sulfonyl urea, mesooxalates, guanidine derivatives have been developed and various preparations containing one of the compounds have been marketed but each of them is of a mere symptomatic treating agent to a hyperglycoplasmia due to the diabetes. It has been known that there may be caused due to the biabetes specific chronic complications such as diabetic cataracts, diabetic neuropathy, diabetic retinopathy, diabetic nephrosis and the like but there is almost no effective agent for curing the complications and thus it may be said that no effective therapeutic system has been established.

Therefore, hitherto, various studies have also been made for developing an effective compound for curing such intractable diseases due to the diabetes but it is the fact that there is almost no success case. As one of the studies, there is a search on an anti- or inhibition substance to the enzymes of aldose reductase, since the enzyme reduces in vivo of human and other animals, aldoses such as glucose and galactose into corresponding polyols such as sorbitol and lactinol and it has been elucidated that said complications will appear when the polyols are accumulated at crystalline lens, peripheral nerve, kidney or the like in patients of diabetes or galactosemia ["Jap. J. Opthalmol." Vol. 20, page 399 (1976), "Int. Congr. Ser. Excerpta Med." Vol. 403, page 594 (1977), and "Metabolism" Vol. 28, page 456 (1979)].

Some of the inventors for this application have studied to find that following spiro-3-heteroazolidine derivatives and salts thereof are effective to the complications due to the diabetes (Jap. Pat. Appln. No. 41234/1985 early opened on Sept. 5, 1986 in Jap. Unexamined Pat. Appln. Gazette No. 200991/1986, which corresponding to U.S. patent application Ser. No. 835,823 and European Pat. Appln. No. 86301530.1, respectively).

$$\underset{\underset{X}{\overset{Z''}{\overset{Y''}{\diagdown}}}}{\overset{U=\overline{\underset{T}{\bigg|}}\underset{V'}{\overset{NH}{\underset{W'}{\bigg|}}=O}}{}}$$

wherein
T is sulfur atom or hydrogen substituted nitrogen atom, U is oxygen atom, sulfur atom or an amino radical, one of V' and W' is hydrogen atom or an alykl group and the other is hydrogen atom, 1H-tetrazol-5-yl radical, —COOR$_6$,
in which R$_6$ is hydrogen atom, an alkyl group, —(CH$_2$CH$_2$O)nCH$_3$ group (n is an integer of 1 to 113) or a substituted phenyl group, $$-CON\underset{R_2}{\overset{R_1}{\diagup}}$$

group,
in which R$_1$ and R$_2$ are same or different independently, each is hydrogen atom, an alkyl group, substituted phenyl group, —(CH$_2$CH$_2$O)nCH$_3$ group (n has the meaning as referred to) or R$_1$ may form a heterocyclic ring together with R$_2$ and nitrogen or oxygen atom, —CH$_2$OR$_3$ group, $$-CH_2N\underset{R_4}{\overset{R_3}{\diagup}}$$

group,
in which R$_3$ and R$_4$ are same or different independently and each is hydrogen atom or an alkyl group,
X is oxygen or sulfur atom, Y'' and Z'' are same or different independently and each is hydrogen atom, a halogen atom, alkyl group, alkoxy group or alkylmercapto group, but there is no case of that one of V' and W' is hydrogen atom and the other is hydrogen atom or an alkyl group, when T is hydrogen substituted nitrogen atom and U is oxygen atom.

SUMMARY OF THE INVENTION

A basic object of the present invention is to provide a novel inhibition substance to aldose reductase to prevent an accumulation of polyols in vivo to, in turn, make prevention and curing of complications of the diabetes.

A specific object of the invention is to provide novel hydantoin derivatives and salts thereof as the inhibition substance to aldose reductase.

Another specific object of the invention is to provide a process for the preparation of the hydantoin derivatives and salts.

A still other specific object of the invention is to provide novel intermediates for preparing the hydantoin derivatives and salts, and a process for the preparation of the intermediates.

According to the invention, the basic and first specific objects can be attained by the hydantoin derivatives of the formula $$\underset{\underset{X}{\overset{Z}{\overset{Y}{\diagdown}}}}{\overset{O=\overline{\underset{HN}{\bigg|}}\underset{V}{\overset{NH}{\underset{W}{\bigg|}}=O}}{}} \quad (I)$$

wherein
one of V and W is hydrogen and the other is a halogenomethyl group, 1H-tetrazol-5-yl radical, —COOR group,
in which R is hydrogen atom, an alkyl group, —(CH$_2$CH$_2$O)nCH$_3$ group (n is an integer of 1 to 113) or substituted phenyl, $$-CON\underset{R_2}{\overset{R_1}{\diagup}}$$

group,
in which R$_1$ and R$_2$ are same or different independently, each is hydrogen atom, an alkyl group, substituted phenyl or —(CH$_2$CH$_2$O)nCH$_3$ group (n has the meaning as referred to) or R$_1$ may form a heterocyclic ring together with R$_2$ and nitogen or oxygen atom, —CH$_2$OR$_3$ group or $$-CH_2N\underset{R_4}{\overset{R_3}{\diagup}}$$

group,
in which R$_3$ and R$_4$ are same or different independently and each is hydrogen atom or an alkyl group,
X is oxygen or sulfur atom, and Y and Z are same or different independently and each is hydrogen atom, halogen atom, alkyl group, alkoxy group, alkylmercapto group, nitro radical or —NHR$_5$ group, in which R$_5$ is hydrogen atom or an acyl group,
and salts thereof.

Namely, it has been confirmed that the hydantoin derivatives shown by Formula I and the salts thereof show an inhibition of aldose reductase, which is better than that of the spiro-3-heteroazolidine derivatives disclosed in said Japanese official gazette and that a toxicity thereof is quite low.

In the compounds of Formula I, the term "alkyl group" may be straight-chain alkyl radicals, branched-chain alkyl radicals or cycloalkyl radicals. As examples for the straight-chain alkyl radicals, one having 1 to 6 carbon atoms, for instance methyl, ethyl, n-propyl, n-butyl, n-pentyl, n-hexyl and the like can be listed. As examples for the branched-chain alkyl radicals, for instance isopropyl, isobutyl, s-butyl, t-butyl and the like can be listed. As examples for the cycloalkyl radicals, one having 3 or more carbon atoms, for instance cyclopropyl, cyclobutyl, cyclopentyl, cyclohexyl and the like can be listed. As examples for the halogenomethyl group, fluoromethyl chloromethyl, bromomethyl, iodomethyl and the like can be listed. The term of "halogen atom" may be fluorine, chlorine, bromine or iodine. The symbol "n" relates to the mean polymerization degree of ethylene glycol part of polyethylene glycol methyl ether. As exemplar values for the mean polymerization degree, 4, 7, 12, 16, 42 and 113 may be listed. As substituents for the substituted phenyl radical, o-, m- or p-chlorine, bromine atoms, methyl, methoxy and hydroxy radicals may be listed. As examples of the radical, when $R_1$ forms the heterocyclic ring together with $R_2$ and nitrogen atom or oxygen atom, pyrrolidinyl, morpholino, piperidino, piperazinyl and the like radicals can be listed. As examples for the alkoxy group and alkylmercapto group, those having a straight-chain alkyl group, for instance methoxy, ethoxy, n-propoxy, n-butoxy, n-pentyloxy, n-hexyloxy and the like as well as methylmercapto, ethylmercapto, n-propylmercapto, n-butylmercapto, n-pentylmercapto, n-hexylmercapto and the like can be listed, or those having a branched-chain alkyl group, for instance isopropoxy, isobutoxy, s-butoxy, t-butoxy and the like as well as isopropylmercapto, isobutylmercapto, s-butylmercapto, t-butylkmercapto and the like can be listed. As examples for the acyl group, acetyl, propanoyl, butanoyl and the like can be listed.

The salts of the hydantoin derivatives mean that acceptable in pharmacological field and with a cation of sodium, potassium, calcium, magnesium or the like.

According to the invention, the compounds of Formula I can be prepared through one of following routes.

ROUTE A

A process wherein a compound of the formula

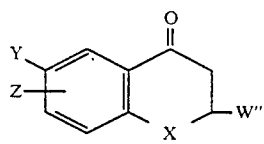

(XI)

wherein X, Y and Z have the meanings as referred to, and W''' is a halogenomethyl group, 1H-tetrazol-5-yl radical, —COOR group,

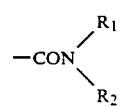

group, —CH$_2$OR$_3$ group or

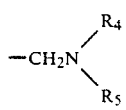

group, in which R, $R_1$ and $R_5$ have the meanings as referred to is reacted with a metal cyanide and ammonium carbonate. The reaction for this route can be shown following formula.

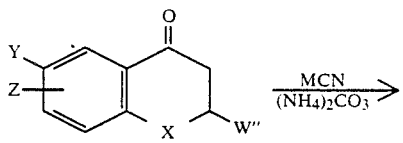

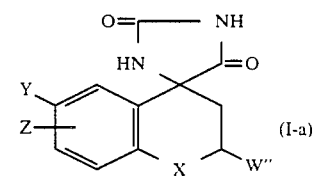

wherein W''', X, Y and Z have the meanings as referred to.

ROUTE B

A compound of the formula

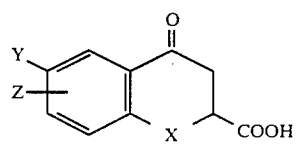

(II)

wherein X, Y and Z have the meanings as referred to is reacted with a metal cyanide and ammonium carbonate as in said Route A to synthesize a compound of the formula

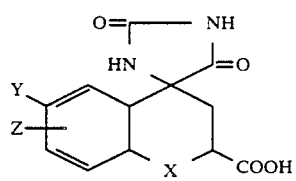

(I-b)

wherein X, Y and Z have the meanings as referred to and then this compound is lead into 2-carboxamide derivatives (I-c), 2-ester derivatives (I-d), 2-hydroxymethyl derivatives (I-e), 2-alkoxymethyl derivatives (I-f), 2-halogenomethyl derivative (I-g) and 2-aminomethyl derivatives (I-h), as shown below and in accordance with manners known per se.

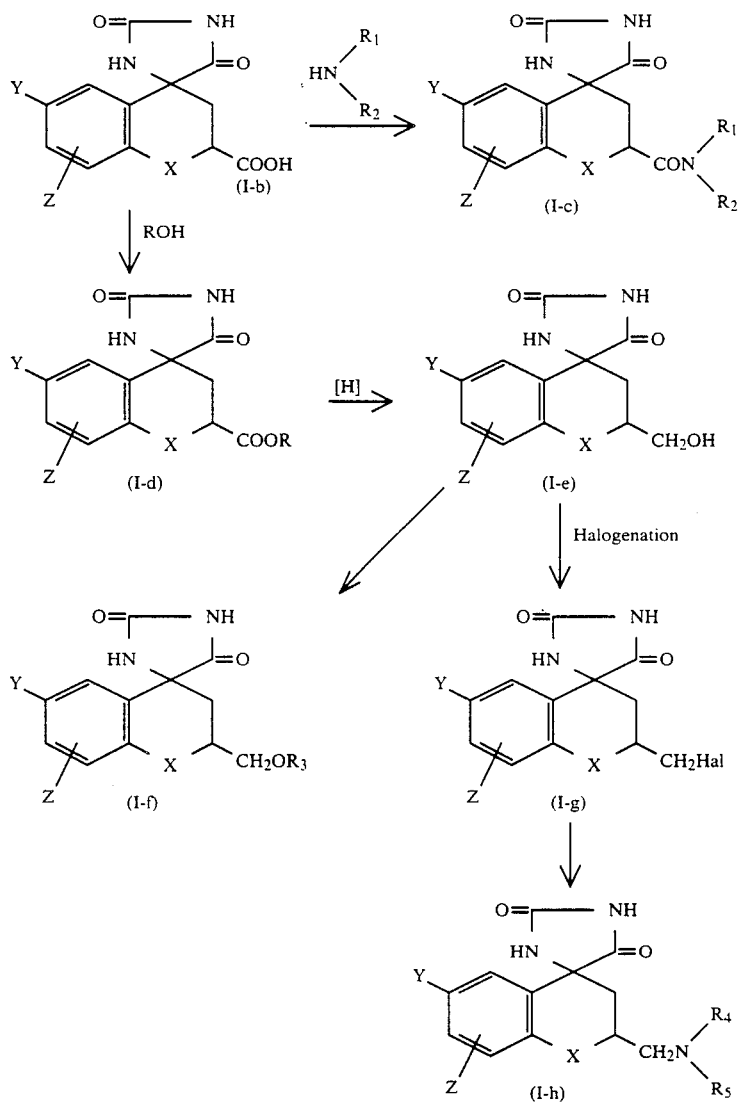

wherein R, $R_1$ to $R_5$, X, Y and Z have the meanings as referred to.

Regarding to the compounds (I) according to the invention, it can be estimated that two kind stereoisomers (diastereomers) will be produced due to 2- and 4-positioned asymmetric carbon atoms in the spiro[4H-1-benzopyran-4,4′-imidazolidine] ring. According to the process shown in said Route A, it has been confirmed that one of the isomers can be predominantly formed, the isomer can be isolated by simple operation of recrystallization, and the isomer shows higher pharmaceutical activity in inhibition of accumuration of sorbitol, galactitol and the like polyols. Namely, in the Route A, a forming ratio between the predominant isomer and the other isomers is about 5:1 to 10:1 and the former shows 10 times or more of the latter in inhibition of polyol accumration.

In case of the Route B, each of single diastereomers of I-c, I-d, I-e, I-f, I-g and I-h can be prepared by using single diastereomer as the raw material, which is predominantly formed among the diastereomer mixture of the compound (I-b).

In both of the Routes A and B, the predominantly formed crystal (single diastereomer) is dl-compound which shows a relatively high activity but the inventors have tried an optical resolution thereof to find that each of the d- and l-compounds has the pharmaceutical activity and that the activity of d-compound is higher than that of the dl-compound in 2 times or more.

There are various methods to obtain optically active d- and l-compounds among the compounds (I), since those can be attained by subjecting the corresponding dl-compound to the optical resolution known per se, but one of preferable methods may be shown below.

A dl-compound among the compound (I) is treated in a conventional manner with a resolution agent such as brucine, cinchonine, quinine and quaternary salts thereof or the like optical active alkaloid, α-phenethylamine (d- and l-compounds), 3-aminomethylpinane (d- and l-compounds) or the like to obtain respective diastereomer salts and then the salts are separated in a conventional manner to obtain the optical active compounds (I). The method will be explained in more detail, as to the case of that cinchonine-methohydoxide or quinine-methohydroxide is employed as the optical resolution agent. dl-compound among the compounds (I) is dissolved in methanol, ethanol, acetone or the like organic solvent, quinine-methohydroxide solution in equivalent amount is added thereto, and then the mixture is concentrated in vacuo to obtain N-methylquinium salt of the corresponding compound, as an amorphous substance. The amorphous substance is dissolved in methanol ethanol, isopropanol, acetone or the like organic solvent and the solution is left to stand to form crystals. The crystals are obtained through a filtration of the solution and subjected to recrystallization to obtain N-methylquinium salt of the d-compound. The salt was treated with hydrochloric acid and recrystallized from an organic solvent in a conventional manner to obtain the desired d-compound (I). While the mother liquor, from which the d-compound was filtered off, is concentrated to obtain N-methylquinium salts of the compounds mainly containing the l-compound and thus the salts are treated with hydrochloric acid to obtain crystals of the compounds containing mainly the l-compound. The crystals are dissolved in methanol, ethanol, acetone or the like organic solvent, cinchonine-methohydrooxide solution in equivalent amount is added thereto, and the mixture is concentrated in vacuo to obtain N-methylcinchonium salts of the compounds containing mainly the l-compound. The salts are dissolved in methanol, ethanol, isopropanol, acetone or the like organic solvent and left to stand to obtain crystals which are recrystallized to obtain N-methylcinchonium salt of the l-compound. The salt is treated with hydrocholoric acid and recrystallized from an organic solvent to obtain the desired l-compound (I).

According to said method, the d-compound is firstly obtained with use of quinine-methohydroxide as the resolution agent and then the l-compound is obtained with use of cinchonine-methohydroxide but this method can also be carried out by firstly obtaining the l-compound with use of cinchonine-methohydroxide and then obtaining the d-compound with use of quinine-methohydroxide.

The d- and l-compounds of compounds (I-c), (I-d), (I-e), (I-f), (I-g) and (I-h) can be obtained by carrying out a similar optical resolution with respect to the compounds (I-b) and (I-e) to obtain corresponding d- and l-compound and then carrying out the synthesis as shown in the reaction formula for the Route B, with use of the d- or l-compound as the raw material.

ROUTE C

A process wherein a compound of the formula

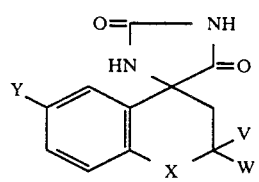

wherein V, W, X and Y have the meanings as referred to, is nitrated in 8-position, if necessary reduced the introduced nitro radical into amino radical and if necessary acylated the amino radical.

The nitration can be carried out in a manner known per se, for instance with use of strong nitric acid under temperature of −30 to room temperature. The reduction of nitro radical into amino radical can also be carried out in conventional manner with hydrogenation in the presence of a suitable catalyst, for instance Pt, Pd, Raney nickel or the like. As the acylating agent, an acid halide, acid anhydride, active ester and the like reactive acid derivatives may be listed.

According to the invention, the second specific object of the invention can be attained by the optical active 3,4-dihydro-4-oxo-2H-1-benzopyran-2-carboxylic acid derivatives of the formula

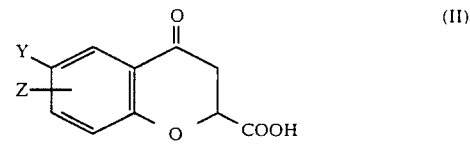

wherein Y' and Z' have the meaning as referred to.

The derivatives which can be employed as the raw material for preparing optical active hydantoin derivatives (I) can be prepared by reacting a compound of the formula

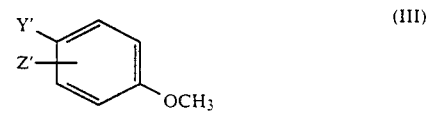

wherein Y' and Z' have the meanings referred to, with maletic anhydride, causing with a base a ring closure of the resulting compound of the formula

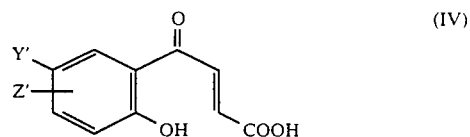

wherein Y' and Z' have the meanings as referred to, activating the resulting compound of the formula

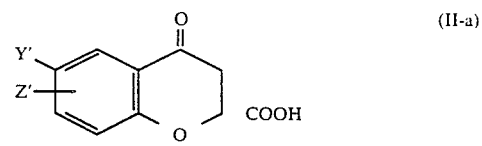

wherein Y' and Z' have the meanings as referred to, reacting the compound with (S)-(−)-1-methylbenzylamine, subjecting the resulting diastereomer mixture of the formula

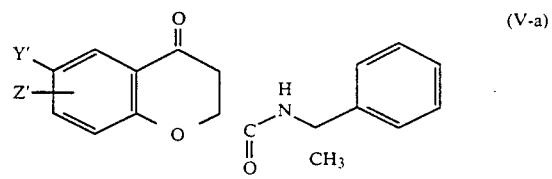

wherein Y' and Z' have the meanings as referred to, to a fractional recrystallization, and then hydrolizing the resulting (d)- and (l)-compounds of the formula

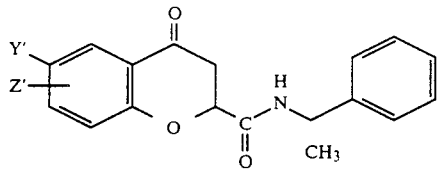

wherein Y' and Z' have the meanings as referred to.

It may, in general, be considered for the synthesis of the compound (IV) to utilize the acylation (Friedel-Crafts reaction) of the phenol derivative of the formula

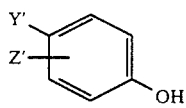

wherein Y' and Z' have the meanings as referred to, with maleic anhydride but no satisfactionary result can be obtained, since undesirable acylation to the oxygen atom of the phenol derivative will preferencially occur. In order to prevent the acylation to the oxygen atom, it necessary to protect the hydroxy radical of the phenol derivative. As the protecting radical, alkyl radical such as methyl radical is selected, in view of a cost and operability therefor. The protection by methyl radical can be easily and quantitiatively carried out by using dimethyl sulfate.

Therefore, in the first step, the anisole derivative (III) formed by protecting hydroxy radical of the phenol derivative is subjected to the Friedel-Crafts acylation with maleic anhydride to form the compound (IV). The reaction conditions depend on the anisole derivative to be selected but are, in general as follows.

It is preferably to use maleic anhydride in more than 1.1 times molar amount to the anisole derivative (III), so that the anisole derivative is fully exhausted. As a solvent, dichloromethane, carbon tetrachloride, 1,2-dichloroethane, carbon disulfide, nitrobenzene or the like may be employed. As a catalyst, Lewis acids such as aluminum chloride, boron trifluoride, boron tribromide and the like may be listed but it is preferable to use aluminum chloride in more than 2 times molar amount to maleic anhydride. The reaction temperature and time depend on the solvent selected but if dichloromethane is employed, the reaction will be completed in 0.5 to 3 hours under reflux temperature. During the reaction, demethylation (removal of protection radical) will occur to obtain the compound (IV) (Yield: 80 to 95%).

As the base to be used in the second step for ring closing the compound (IV) to make into the racemic, 3,4-dihydro-4-oxo-2H-1-benzopyran-2-carboxylic acid derivative (II-a), sodium carbonate, potassium carbonate, sodium bicarbonate, sodium hydroxide, potassium hydroxide or the like may be employed but sodium bicarbonate is especially preferable among them. An amount of the base is sufficiently by 1.01 to 2.0 equivalents. As a solvent, water, water/ethanol, water/methanol or the like polar solvent may be listed but water is mostpreferable. There is no ground to give a limitation on reaction temperature and the reaction smoothly proceeds at a temperature ranging from 10° to 100° C. The reaction completes by about 10 minutes, when the reaction is carried out at 100° C. The desired compound (II-a) can be obtained in relatively high yield of 90 to 95% by extracting same with a suitable organic solvent such as ethyl acetate, after completion of the reaction.

In the third step for activating the compound (II-a) and causing the reaction with (S)-(−)-1-methylbenzylamine to make into the diastereomer mixture (V-a), the activation can be carried out by converting the compound into its acid halide, in a conventional manner. As a halogenation agent therefor, thionyl chloride, phosphoric pentachloride or the like can be employed in an amount of 1 to 3 equivalent one. The activating reaction will proceed smoothly without use any solvent but as the solvent, benzene, dichloromethane, dichloroethane or the like may be employed. There is no limitation on the reaction temperature and if a solvent is employed, a temperature between 10° C. and boiling point of the solvent may be employed. After completion of the reaction, the solvent or excessive halogenation agent is distilled out to quantitatively obtain the activated compound (V) of acid halide, for instance acid chloride. The reaction between this acid halide and (S)-(−)-1-methylbenzylamine can be carried out by using the reactants in equimolar amount in a suitable solvent and in the presence of a base. As the base for this reaction, triethylamine, pyridine and the like may be listed but triethylamine is more preferable. As the solvent, dichloromethane, dichloroethane, N,N-dimethylformamide and the like may be listed but dichloromethane is more preferable. The reaction will, in general, be completed for about 1 hour, when the reaction is carried out at a temperature between 0° and 20° C. After completion of the reaction, the reaction mixture is washed by water to obtain the diastereomer mixture (V-a) with yield of 90 to 100%.

In the fourth step for fractionally recrystallizing the diastereomer mixture (V-a) to convert same into the optical active compound (V), ethanol and methanol and the like alcohols may be listed as the recrystallization solvent but ethanol is preferable, which is used 5 to 20 times in amount. By carrying out the recrystallization operation twice, (d)-type compound (V) having an optical purity of more 90% e.e. can be obtained with a higher yield of 70 to 80%. While, a similar recrystallization operation is carried out twice with use of the mother liquid to obtain (l)-type compound (V) having an optical purity of more 90% e.e. and with a higher yield of 70 to 80%.

In the last of fifth step for hydrolyzing the compound (V) to convert the same into the desired optical active compound of 3,4-dihydro-4-oxo-2H-1-benzopyran-2-carboxylic acid, as the hydrolyzing agent, an acid, for instance hydrochloric acid, bromic acid, sulfuric acid or the like mineral acid may be employed but hydrochloric acid is more preferable. As the solvent, methanol, ethanol, dioxane, acetic acid or the like may be employed but dioxane is more preferable. There is no specific limitation on the reaction temperature and time but the reaction will be completed for about 20 hours, when it carried out at 100° C. After completion of the reaction, an extraction is carried out with use of dichloromethane or the like organic solvent to obtain the desired compound (II) having an optical purity of more 99% e.e. and with a higher yield of 85 to 95%.

The optical active hydantoin derivatives (I-b, I-c, I-d, I-e, I-f, I-g and I-h) can be synthesized by using the resulting optical active compound (II) as the raw material. Namely, a reaction of the optical active compound (II), metal cyanide and ammonium carbonate gives the optical active hydantoin compound (I-h). And, by using the resulting (d)- or (l)-type compound (I-b) as the raw material and carrying out the synthesis in accordance with the Route B, (d)- and (l)-type compounds of I-c, I-d, I-e, I-f, I-g and I-h can be obtained, respectively.

The d-type amido derivative (I-c) having a strong aldose reductase inhibition can be synthesized with a higher yield by using d-type compound (II) as raw material therefor. The d-type hydantoin derivative (I-b) derived from d-type compound (II) can be converted with a higher yield (97.1%) into d-type ester derivative (I-d). By reacting the resulting compound (I-d) with a compound of the formula

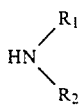

wherein $R_1$ and $R_2$ have the meanings as referred to, in the presence or absence of a catalyst, the d-type compound (I-c) can be obtained with a higher yield of more than 90%. This method is quite useful for synthesizing the compound (I-c), since the yield thereof is higher than that in Route B wherein the compound is synthesized through the compound (I-b). Therefore, this method is named as Route D.

ROUTE D

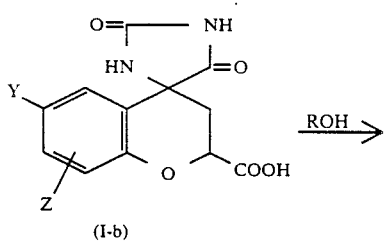

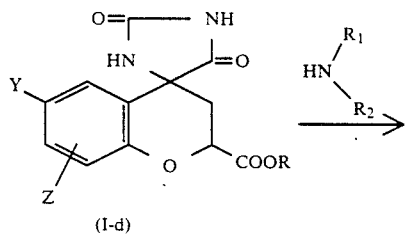

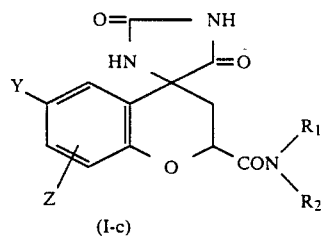

As a solvent for amidizing reaction of the compound (I-d), methanol, ethanol, n-propanol or the like lower alcohol, tetrahydrofuran, dioxane or the like cycroether, N,N-dimethylformamide or the like can be used. If necessary, ammonium chloride, sodium methoxide, sodium amide, butyllithium, sodium hydride or the like may be employed as a catalyst.

The reaction can be carried out at a temperature between 0° to 100° C. In case of the reaction with a lower amine, the reaction under conditions of room temperature, in methanol and in the absence of catalyst gives a especially preferable result.

In the manner similar to the above, l-type amido derivative (I-c) can also be obtained with a higher yield. In accordance with this Route D, by starting from l-type compound (II) as raw material therefor.

EFFECTS OR ADVANTAGES OF THE INVENTION

The compounds (I) and salts thereof according to the invention, especially d-type as well as dl-type compounds and more particularly the d-type compounds show an excellent inhibition to aldose reductase and thus useful as an effective ingredient for medicines for preventing or curing complications of diabetes. Certain compounds (I) show a quite low toxicity ($LD_{50}$=more than 500 mg/kg), when the compound is administered in oral route.

FORM AS MEDICINES AND DOSING AMOUNT

There is no specific limitation, when the compound or salt according to the invention will be made into a medicine containing at least one of the compounds or salts, as effective ingredient. Therefore, the medicine may be of a solid form such as tablet, pill, capsule, powder, granules and suppository or a liquid form such as solution, suspension or emulsion, together with a conventional additive(s) and/or a carrier(s).

A dosing amount of the compound or salt for human depends on kind of the compound or salt per se to be selected, condition of illness, age of the patient, form of the medicine and other factors but in case for an adult, 0.1 to 500 mg/day and more particularly 1 to 150 mg/day are preferable.

DETAILED DESCRIPTION OF PREFERRED EMBODIMENTS

The invention will now be further explained with reference to Manufacturing Examples of the compounds and salts, Pharmacological Test Examples as well as Prescriptional Examples.

EXAMPLE 1 dl-6-fluoro-2,3-dihydro-2',5'-dioxo-spiro[4H-1-benzopyran-4,4'-imidazolidine]-2-carboxylic acid A mixture of potassium cyanide (16.1 g, 0.248 mol), ammonium carbonate (71.4 g, 0.744 mol) and dl-6-fluoro-3,4-dihydro-4-oxo-2H-1-benzopyran-2-carboxylic acid 26.0 g, 0.124 mol) in 237 ml of water was stirred at 65°–70° C. for 24 hours, and then at 80°–90° C. for 15 minutes. The reaction mixture was cooled to room temperature and acidified with concentrated hydrochloric acid. Resulting crystals were obtained through a filtration to give 30.6 g of a diastereomer mixture of 6-fluoro-2,3-dihydro-2',5'-dioxo-spiro[4H-1-benzopyran-4,4'-imidazolidine]-2-carboxylic acid (5:1 mixture) as pale yellow crystals. The crystals were recrystallized from water to give 20.4 g (58.8%) of the subject desired compound.

The compound was a single diastereomer without containing another diastereomer.

melting point: 294°–298° C. (dec.).

IR spectrum ($\nu_{max}^{KBR}$) cm$^{-1}$: 1770, 1750, 1720.

NMR spectrum (DMSO-$d_6$) δ ppm: 1.88–2.80 (2H, m), 5.23 (1H, dd), 6.83–7.38 (3H, m), 8.37 (1H, br.s), 11.07 (1H, br.s).

Mass spectrum (EI/DI) m/z: 280 (M+), 262, 234, 219.

Elementary analysis: $C_{12}H_9FN_2O_5$: Cal.: C, 51.43; H, 3.24; N, 10.00. Found: C, 51.15; H, 3.28; N, 9.98.

From the mother liquor, the other diastereomer of the subject compound was obtained.

In the evaluation of these diastereomers on the ability of reduction or inhibition of polyol increase in sciatic nerve of galactosemic rats, the potency of the major diastereomer (firstly obtained one) was higher than that of the minor diastereomer.

EXAMPLE 2 dl-6-Fluoro-2,3-dihydro-2',5'-dioxo-spiro[4H-1-benzopyran-4,4'-imidazolidine]-2-carboxamide (a) To a solution of dl-6-fluoro-2,3-dihydro-2',5'-dioxo-spiro[4H-1-benzopyran-4,4'-imidazolidine]-2-carboxylic acid (150 g, 0.53 mol) (obtained through the process as described in Example 1) in 1.0 liter of anhydrous pyridine, silicon tetrachloride (66.6 g, 0.392 mol) was added below 10° C. After stirring the solution for 15 minutes at room temperature, dry ammonia gas was introduced in excess amount below 10° C.

The mixture was stirred for 12 hours at room temperature and then poured into 3.0 liter of methanol. Undissolved matter was filtered off and the filtrate was evaporated to dryness. To the residue, 1.2 liter of water were added. The mixture was stirred for an hour at room temperature. Resulting precipitate was obtained through a filtration and recrystallized from methanol to give 110 g (73.2%) of the subject desired compound.

Melting point: 286°–300° C. (dec.).

IR spectrum ($\nu_{max}^{KBR}$) cm$^{-1}$: 1770, 1720, 1670.

NMR spectrum (DMSO-d$_6$) δ ppm: 1.83–2.67 (2H, m), 5.17 (1H, dd), 6.93–7.33 (3H, m), 7.57, 7.80 (1H, br.s), 8.47 (1H, br.s), 11.07 (1H, br.s).

Mass spectrum (EI/DI) m/z: 279 (M+), 262, 235, 219.

Elementary analysis: $C_{12}H_{10}FN_3O_4$: Cal.: C, 51.62; H, 3.61; N, 15.05. Found: C, 51.79; H, 3.58; N, 14.98.

(b) To a solution of the diastereomer mixture (5:1) of 6-fluoro-2,3-dihydro-2',5'-dioxo-spiro[4H-1-benzopyran-4,4'-imidazolidine]-2-carboxylic acid (29.9 g, 107 mmol) (obtained through the process as described in Example 1) in 320 ml of anhydrous pyridine, silicon tetrachloride (20.7 g, 122 mmol) and dry ammonia gas were added as described in said Item (a) and the similar operation was carried out to obtain crystals. The crystals were recrystallized from ethanol to give colorless one (14.4 g, 48.5%) having physical properties same with those obtained in said Item (a).

From the mother liquor, further, another diastereomer of the subject compound was obtained, which has following physical properties.

Melting point: 285°–295° C. (dec.).

IR spectrum ($\nu_{max}^{KBR}$) cm$^{-1}$: 1765, 1724, 1660.

NMR spectrum (DMSO-d$_6$) δ ppm: 1.95–2.68 (2H, m), 4.55 (1H, dd), 6.83–7.48 (3H, m), 7.58, 7.81 (2H, br.s), 8.98 (1H, br.s), 11.18 (1H, br.s).

Mass spectrum (EI/DI) m/z: 279 (M+), 236, 193, 192, 165.

Elementary analysis: $C_{12}H_{10}FN_3O_4$: Cal.: C, 51.62; H, 3.61; N, 15.05. Found: C, 51.57; H, 3.62; N, 15.01.

In the evaluation of these diastereomers on the ability of reduction or inhibition of polyol increase in sciatic nerve of galactosemic rats, the activity of the former crystals having the melting point of 286°–300° C. (dec.) was more than 10 times in comparison with that of the latter crystals having the melting point of 285°–295° C. (dec.).

EXAMPLE 3

Optical resolution of dl-6-fluoro-2,3-dihydro-2',5'-dioxo-spiro[4H-1-benzopyran-4,4'-imidazolidine]-2-carboxamide (a) Preparation of d-6-fluoro-2,3-dihydro-2',5'-dioxo-spiro[4H-1-benzopyran-4,4'-imidazolidine]-2-carboxamide To a suspension of dl-6-fluoro-2,3-dihydro-2',5'-dioxo-spiro[4H-1-benzopyran-4,4'-imidazolidine]-2-carboxamide having the melting point of 286°–300° C. (dec.) (10.0 g, 35.8 mmol) (obtained through the process as described in Example 2) in 500 ml of methanol, an aqueous quinine methohydroxide solution (36.0 mmol) [J. Am. Chem. Soc., Vol. 63, page 1368 (1941)] was added dropwise under stirring in an ice bath. After stirring the mixture at room temperature for 2 hours, the mixture was dissolved in 150 ml of ethanol. The solution was concentrated to the volume of 100 ml under reduced pressure and then allowed to stand for 2 days.

Resulting crystals were obtained through a filtration and recrystallized from ethanol to give 5.02 g of N-methyl-quinium d-6-fluoro-2,3-dihydro-2',5'-dioxo-spiro[4-1-benzopyran-4,4'-imidazolidine]-2-carboxamide salt.

Melting point: 240°–241° C. (dec.).

$[\alpha]_D^{20}$: −14.3° (methanol).

Elementary analysis: $C_{33}H_{36}FN_5O_6$: Cal.: C, 64.17; H, 5.87; N, 11.34. Found: C, 63.82; H, 5.87; N, 11.33.

The salt (4.87 g, 7.74 mmol) was dissolved in the mixture of 17 ml of ethanol and 4.1 ml of water. To the solution under stirring in an ice bath, 8.0 ml of 1N-hydrochloric acid solution were added and the mixture was stirred at room temperature for an hour. The reaction mixture was evaporated in vacuo to give crystalline mass, in which 97 ml of water were added.

After stirring the mixture at room temperature overnight, crystals deposited out therein were obtained through a filtration and recrystallized from ethanol to give 1.30 g of d-6-fluoro-2,3-dihydro-2',5'-dioxo-spiro[4H-1-benzopyran-4,4'-imidazolidine]-2-carboxamide.

Melting point: 290°–291° C. (dec.).

$[\alpha]_D^{20}$: +167° (methanol).

Elementary analysis: $C_{12}H_{10}FN_3O_4$: Cal.: C, 51.62; H, 3.61; N, 15.05. Found: C, 51.73; H, 3.51; N, 14.99.

(b) Preparation of l-6-fluoro-2,3-dihydro-2',5'-dioxo-spiro[4H-1-benzopyran-4,4'-imidazolidine]-2-carboxamide The mother liquor, which was the filtrate after the filtration of the primary crystalline mass of N-methylquinium d-6-fluoro-2,3-dihydro-2',5'-dioxo-spiro[4H-1-benzopyran-4,4'-imidazolidine]-2-carboxamide salt, was evaporated in vacuo to dryness. Resulting amorphous was dissolved in the mixture of 40 ml of ethanol and 10 ml of water and then 19 ml of 1N-hydrochloric acid solution were added dropwise to the solution under stirring in an ice bath. After stirring at room temperature for an hour, the solution was evaporated in vacuo to dryness. To the residue, 220 ml of water were added and the solution was stirred at room temperature overnight.

Resulting crystals (4.88 g) deposited out therein were obtained through a filtration. To a suspension of the crystals (2.84 g) in 100 ml of ethanol under stirring in an ice bath, an aqueous cinchonine methohydroxide solution (11.0 mmol) [J. Am. Chem. Soc., Vol. 41, page 2090 (1919)] was added dropwise. After stirring at room temperature for 2 hours, the solution was evaporated in vacuo to give an amorphous residue which was dissolved in 28 ml of isopropyl alcohol, followed by allowing to stand for 2 days. Resulting crystals deposited out therein were obtained through a filtration and recrystallized from ethanol to give 2.49 g of N-methyl-cinchonium 1-6-fluoro-2,3-dihydro-2',5'-dioxo-spiro[4H-1-benzopyran-4,4'-imidazolidine]-2-carboxamide salt.

Melting point: 242°–243° C. (dec.).

$[\alpha]_D^{20}$: +20.1° (methanol).

Elementary analysis: $C_{32}H_{34}FN_5O_5$: Cal.: C, 65.40; H, 5.83; N, 11.92. Found: C, 65.07; H, 5.84; N, 11.82.

The salt (2.49 g, 4.23 mmol) was dissolved in the mixture of 10 ml of ethanol and 2.0 ml of water. To the solution under stirring in an ice bath, 4.5 ml of 1N-hydrochloric acid solution were added dropwise and the mixture was stirred at room temperature for an hour. The reaction mixture was evaporated in vacuo to give crystalline mass, to which 35 ml of water were added.

After stirring the mixture at room temperature overnight, crystals deposited out therein were obtained through a filtration and recrystallized from ethanol to give 880 mg of 16-fluoro-2,3-dihydro-2',5'-dioxo-spiro[4H-1-benzopyran-4,4'-imidazolidine]-2-carboxamide.

Melting point: 290°–293° C. (dec.).

$[\alpha]_D^{20}$: −169° (methanol).

Elementary analysis: $C_{12}H_{10}FN_3O_4$: Cal.: C, 51.62; H, 3.61; N, 15.05. Found: C, 51.69; H, 3.52; N, 14.99.

EXAMPLE 4 dl-6-Fluoro-2,3-dihydro-2',5'-dioxo-spiro[1-benzopyran-4,4'-imidazolidine]-2-carboxylic acid methyl ester To a solution of dl-6-fluoro-2,3-dihydro-2',5'-dioxo-spiro[[4H-1-benzopyran-4,4'-imidazolidine]-2-carboxylic acid (20.4 g, 72.9 mmol) (obtained through the process as described in Example 1) in 765 ml of methanol, 20.0 ml of concentrated sulfuric acid were added. The mixture was refluxed for 1.5 hours and then cooled to room temperature. Crystals deposited out therein were obtained through a filtration and dried to give 20.0 g (93.4%) of the subject desired compound.

Melting point: 291° C.

IR spectrum ($\nu_{max}^{KBR}$) $cm^{-1}$: 1790, 1745, 1730.

NMR spectrum (DMSO-$d_6$) δ ppm: 1.92–2.85 (2H, m), 3.80 (3H, s), 5.40 (1H, dd), 7.00–7.43 (3H, m), 8.43 (1H, br.s), 11.10 (1H, br.s).

Mass spectrum (EI/DI) m/z: 294 (M+), 262, 234, 192, 164, 137.

Elementary analysis: $C_{13}H_{11}FN_2O_5$: Cal.: C, 53.06; H, 3.77; N, 9.52. Found: C, 53.07; H, 3.62; N, 9.56.

EXAMPLE 5 dl-6-Fluoro-2,3-dihydro-2-hydroxymethyl-spiro[4H-1-benzopyran-4,4'-imidazolidine]-2',5'-dione To a suspension of lithium aluminum hydride (2.30 g, 0.06 mol) in 100 ml of tetrahydrofuran, a solution of dl-6-fluoro-2,3-dihydro-2',5'-dioxo-spiro[4H-1-benzopyran-4,4'-imidazolidine]-2-carboxylic acid methyl ester (11.7 g, 0.04 mol) (obtained through the process as described in Example 4) in 100 ml of tetrahydrofuran was added at 5° C. After stirring the mixture for 20 hours at room temperature (15°–20° C.), the reaction mixture was poured onto 300 ml of cracked ice under stirring. While cooling the solution (10°–15° C.), the solution was acidified to pH 1 by adding concentrated hydrochloric acid and extracted with 400 ml of ethyl acetate. The organic layer was washed with water, dried over anhydrous sodium sulfate, filtered and evaporated in vacuo to give a solid. The solid was recrystallized from methanol to give 8.70 g (82.0%) of the subject desired compound.

Melting point: 224°–225° C. (dec.).

IR spectrum ($\nu_{max}^{KBr}$) $cm^{-1}$: 3360, 1760, 1720.

NMR spectrum (DMSO-$d_6$) δ ppm: 1.70–2.40 (2H, m), 3.50–3.86 (2H, m), 4.50–4.96 (1H, m), 4.50–5.20 (1H, m), 6.80–7.47 (3H,m), 8.46 (1H, br.s), 11.00 (1H, br.s).

Mass spectrum (EI/DI) m/z: 266 (M+), 248, 228.

Elementary analysis: $C_{12}H_{11}FN_2O_4$: Cal.: C, 54.14; H, 4.16; N, 10.52. Found: C, 53.98; H, 4.34; N, 10.35.

EXAMPLE 6

Optical resolution of dl-6-Fluoro-2,3-dihydro-2-hydroxymethyl-spiro[4H-1-benzopyran-4,4'-imidazolidine]-2',5'-dione (a) Preparation of d-6-fluoro-2,3-dihydro-2-hydroxymethyl-spiro[4H-1-benzopyran-4,4'-imidazolidine]-2',5'-dione dl-6-fluoro-2,3-dihydro-2-hydroxymethyl-spiro[4H-1-benzopyran-4,4'-imidazolidine]-2',5'-dione (25.0 g, 93.9 mmol) (obtained through the process as described in Example 5) was dissolved in 2.5 liter of ethanol and to the resulting solution, an aqueous quinine methohydroxide solution (96.1 mmol) was added dropwise, under cooling in an ice bath. After stirring the mixture at room temperature for an hour, the solvent was evaporated in vacuo to give 66.0 g of the residue, which was recrystallized from methanol twice to give 16.4 g of N-methyl-quinium d-6-fluoro-2,3-dihydro-2-hydroxymethyl-spiro[4H-1-benzopyran-4,4'-imidazolidine]-2',5'-dione salt.

Melting point: 235°–237° C. (dec.).

$[\alpha]_D^{20}$: +5.7° (methanol).

Elementary analysis: $C_{33}H_{37}FN_4O_6$: Cal.: C, 65.55; H, 6.17; N, 9.27. Found: C, 65.64; H, 6.33; N, 9.28.

The salt (16.0 g, 26.5 mmol) was added to the mixture of 610 ml of ethyl acetate and 17 ml of water, and then 17 ml of 16% aqueous solution of hydrochloric acid were added dropwise to the mixture under stirring same vigously in an ice bath. After stirring the mixture for 30 minutes, the organic layer was separated from the aqueous layer, and the aqueous layer was further extracted with ethyl acetate. Both of ethyl acetate layers were combined together, dried over anhydrous sodium sulfate and evaporated in vacuo to dryness. The residue was recrystallized from ethanol to give 6.32 1 g of d-6-fluoro-2,3-dihydro-2-hydroxymethyl-spiro-[4H-1-benzopyran-4,4'-imidazolidine]-2',5'-dione.

Melting point: 188°–189° C.

$[\alpha]_D^{20}$: +222° (methanol).

Elementary analysis: $C_{12}H_{11}FN_2O_4$: Cal.: C, 54.14; H, 4.16; N, 10.52. Found: C, 54.29; H, 4.25; N, 10.53.

(b) Preparation of 1-6-fluoro-2,3-dihydro-2-hydroxymethyl-spiro[4H-1-benzopyran-4,4'-imidazolidine]-2',5'-dione.

The mother liquor, which was the filtrate after the filtration of the primary or predominant crystalline mass of N-methyl-quinium d-6-fluoro-2,3-dihydro-2-hydroxymethyl-spiro[4H-1-benzopyran-4,4'-imidazolidine]-2',5'-dione salt, was evaporated i vacuo to dryness. To the residue, 1.25 liter of ethyl acetate and 35 ml of water were added dropwise to the mixture under stirring same vigously in an ice bath. After stirring the mixture for 30 minutes, the organic layer was separated from the aqueous layer, and the aqueous layer was further extracted with ethyl acetate. Both of ethyl acetate layers were combined together, dried over anhydrous magnesium sulfate and evaporated in vacuo to give 12.0 g of crystalline mass.

The crystalline mass (11.3 g, 42.4 mmol) was dissolved in 200 ml of ethanol, and an aqueous cinchonine methohydroxide solution (46.4 mmol) was added to the solution under stirring in an ice bath. After stirring the mixture at room temperature for an hour, the solvent was evaporated in vacuo to give the residue, which was crystallized from ethanol. The resulting crystals were obtained through a filtration and recrystallized from methanol to give 15.5 g of N-methyl-cinchonium 1-6-fluoro-2,3-dihydro-2-hydroxymethyl-spiro[4H-1-benzopyran-4,4'-imidazolidine]-2',5'-dione salt.

Melting point: 244°–246° C. (dec.).

$[\alpha]_D^{20}$: +3.8° (methanol).

Elementary analysis: $C_{33}H_{37}FN_4O_5$: Cal.: C, 66.88; H, 6.14; N, 9.75. Found: C, 67.04; H, 6.32; N, 9.82.

The salt (15.0 g, 26.1 mmol) was added to the mixture of 610 ml of ethyl acetate and 17 ml of water, and then 17 ml of 16% aqueous solution of hydrochloric acid were added dropwise to the mixture under stirring same vigously in an ice bath. After stirring at room temperature the mixture for 30 minutes, the organic layer was separated from the aqueous layer, and the aqueous layer was further extracted with ethyl acetate. Both of ethyl acetate layers were combined together, dried over anhydrous sodium sulfate and evaporated in vacuo to dryness. The residue was recrystallized from ethanol to give 6.3 g of 1-6-fluoro-2,3-dihydro-2-hydroxymethyl-spiro[4H-1-benzopyran-4,4'-imidazolidine]-2',5'-dione.

Melting point: 177°–189° C. (dec.).

$[\alpha]_D^{20}$: −231° (methanol).

Elementary analysis: $C_{12}H_{11}FN_2O_4$; Cal.: C, 54.14; H, 4.16; N, 10.52. Found: C, 54,31; H, 4.15; N, 10.54.

EXAMPLE 7 dl-2-Chloromethyl-6-fluoro-2,3-dihydro-spiro[4H-1-benzopyran-4,4'-imidazolidine]-2',5'-dione To a sodium of dl-6-fluoro-2,3-dihydro-2-hydroxymethyl-spiro [4H-1-benzopyran-4,4'-imidazolidine]-2',5'-dione (2.66 g, 10 mmol) (obtained through the process as described in Example 5) in 20 ml of N,N-dimethylformamide, thionylchloride (1.19 ml, 10 mmol) was added. The solution was stirred at room temperature for 2.0 hours and further at 80°–85° C. for 4 hours. After cooling, the reaction mixture was poured onto 100 ml of cracked ice and resulting precipitate was obtained through a filtration. The precipitate was partitioned between 70 ml of ethyl acetate and 50 ml of water. The organic layer was dried over anhydrous sodium sulfate and the solvent was evaporated in vacuo to give s pale yellow solid which was chromatographed on silica gel, eluted with ethyl acetate/n-hexane (1:1) to give 2.42 g (85.1%) of the subject desired compound.

Melting point: 212°–214° C.

NMR spectrum (DMSO-d₆) δ ppm: 1.86–2.43 (2H, m), 3.90–4.30 (2H, m), 4.76–5.23 (1H, m), 6.90–7.40 (3H, m), 8.46 (1H, br.s), 10.00–11.50 (1H, br.s).

Mass spectrum (EI/DI) m/z: 284 (M⁺), 248, 219, 205, 177, 164, 137.

Elementary analysis: $C_{12}H_{10}ClFN_2O_3$: Cal.: C, 50.63; H, 3.54; N, 9.84. Found: C, 50,77; H, 3.40; N, 9.71.

EXAMPLE 8 d-2-Chloromethyl-6-fluoro-2,3-dihydro-spiro[4H-1-benzopyran-4,4'-imidazolidine]-2',5'-dione To a solution of d-6-fluoro-2,3-dihydro-2-hydroxymethyl-spiro[4H-1-benzopyran-4,4'-imidazolidine]-2',5'-dione (600 mg, 2.25 mmol) (obtained through the process as described in Example 6-a) in 3.00 ml of N,N-dimethylformamide, thionylchloride (0.17 ml, 2.39 mmol) was added. The solution was stirred at room temperature for 3.0 hours and further at 80° C. for 3.0 hours. Thereafter, the operation as described in Example 7 was carried out to give 461 mg (71.8%) of the subject desired compound.

Melting point: 239°–240° C.

$[\alpha]_D^{20}$: +216° (methanol).

Elementary analysis: $C_{12}H_{10}ClFN_2O_3$: Cal.: C, 50.63; H, 3.54; N, 9.84. Found: C, 50.72; H, 3.49; N, 9.94.

EXAMPLE 9

1-2-Chloromethyl-6-fluoro-2,3-dihydro-spiro[4H-1-benzopyran-4,4'-imidazolidine]-2',5'-dione The operation as described in Example 8 was repeated except that 1-6-fluoro-2,3-dihydro-2-hydroxymethyl-spiro[4H-1-benzopyran-4,4'-imidazolidine]-2',5'-dione (600 mg, 2.25 mmol) (obtained through the process as described in Example 6-b) was employed as the starting material in lieu of the corresponding d-type compound. In this case, 492 mg (76.6%) of the subject compound were obtained.

Melting point: 239°–240° C.

$[\alpha]_D^{20}$: −217° (methanol).

Elementary analysis: $C_{12}H_{10}ClFN_2O_3$; Cal.: C, 50.63; H, 3.54; N, 9.84. Found: C, 50.46; H, 3.34; N, 9.86.

EXAMPLE 10 dl-2-Bromomethyl-6-fluoro-2,3-dihydro-spiro[4H-1-benzopyran-4,4'-imidazolidine]-2',5'-dione To a solution of dl-6-fluoro-2,3-dihydro-2-hydroxymethyl-spiro[4H-1-benzopyran-4,4'-imidazolidine]-2',5'-dione (3.6 g, 13.5 mmol) (obtained through the process as described in Example 5) in 28.0 ml of N,N-dimethylformamide, thionylbromide (3.47 g, 16.7 mmol) was added below 10° C. The mixture was stirred at room temperature for 2.0 hours and further stirred for 1.5 hours at 80° C. After cooling, the reaction mixture was poured onto 40 ml of cracked ice. Resulting aqueous solution was stirred for 30 minutes at room temperature and extracted with ethyl acetate. The organic layer was washed with water, dried over anhydrous sodium sulfate, filtered and evaporated in vacuo to give a solid. The solid was recrystallized from the mixture of acetone and n-hexane to give 3.40 g (77.3%) of the subject desired compound.

Melting point: 209°–211° C. IR spectrum ($\lambda_{max}^{KBr}$) cm⁻¹: 1780, 1740, 1495.

NMR spectrum (DMSO-d₆) δ ppm: 1.87–2.43 (2H, m), 3.73–4.03 (2H, m), 4.73–5.20 (1H, m), 6.83–7.47 (3H, m), 8.53 (1H, br.s), 11.05 (1H, br.s).

Elementary analysis: $C_{12}H_{10}BrFN_2O_3$: Cal.: C, 43.79; H, 3.06; N, 8.51. Found: C, 43.67; H, 3.02; N, 8.48.

EXAMPLE 11 d-2-Bromomethyl-6-fluoro-2,3-dihydro-spiro[4H-1-benzopyran-4,4'-imidazolidine]-2',5'-dione To a solution of d-6-fluoro-2,3-dihydro-2-hydroxymethyl-spiro[4H-1-benzopyran-4,4'-imidazolidine]-2',5'-dione (2.00 g, 7.51 mmol) (obtained through the process as described in Example 6-a) in 15.0 ml of N,N-dimethylformamide, thionylbromide (0.64 g, 8.27 mmol) was added. The mixture was stirred at room temperature for 2.0 hours and then refluxed for 1.5 hours. The reaction mixture was poured onto 67.0 ml of cracked ice and extracted with ethyl acetate. The organic layer was washed with water, dried over anhydrous sodium sulfate, filtered and evaporated in vacuo. The resulting residue was chromatographed on silica gel, eluted with ethyl acetate/n-hexane (1:1) to give crystals. The crystals were recrystallized from ethyl acetate to give 1.74 g (70.4%) of the subject desired compound.

Melting point: 226°–227° C.
$[\alpha]_D^{20}$: +193° (methanol).
Elementary analysis: $C_{12}H_{10}BrFN_2O_3$: Cal.: C, 43.79; H, 3.06; N, 8.51. Found: C, 43.75; H, 2.80; N, 8.63.

EXAMPLE 12 l-2-Bromomethyl-6-fluoro-2,3-dihydro-spiro[4H-1-benzopyran-4,4'-imidazolidine]-2',5'-dione The operation as described in Example 11 was repeated except that l-6-fluoro-3,4-dihydro-2-hydroxymethyl-spiro[4H-1-benzopyran-4,4'-imidazolidine]-2',5'-dione (2.00 g, 7.51 mmol) (obtained through the process as described in Example 6-b) was employed as the starting material in lieu of the corresponding d-type compound. In this case, 1.81 g (73.3%) of the subject desired compound were obtained.

Melting point: 226°–227° C.
$[\alpha]_D^{20}$: −193° (methanol)
Elementary analysis: $C_{12}H_{10}BrFN_2O_3$: Cal.: C, 43.79; H, 3.06; N, 8.51. Found: C, 43.50; H, 2.81; N, 8.53.

EXAMPLE 13 dl-6-Fluoro-2-fluoromethyl-2,3-dihydro-spiro[4H-1-benzopyran-4,4'-imidazolidine]-2',5'-dione To 15 ml of anhydrous tetrahydrofuran under argon atmosphere, diethylaminosulfur trifluoride (4.09 g, 25 mmol) and a solution of dl-6-fluoro-2,3-dihydro-2-hydroxymethyl-spiro[4H-1-benzopyran-4,4'-imidazolidine]-2',5'-dione (3.99 g, 15 mmol) (obtained through the process as described in Example 5) in 80 ml of anhydrous tetrahydrofuran were added dropwise below −50° C. The mixture was then warmed to room temperature (25° C.) and stirred for 4.5 hours at room temperature (25°–30° C.). The solvent in the mixture was evaporated in vacuo and the residue was partitioned between water and ethyl acetate. The organic layer was washed with water, dried over anhydrous sodium sulfate, filtered and evaporated in vacuo to dryness. The remaining residue was chromatographed on silica gel, eluted with ethyl acetate/n-hexane (1:1) to give 1.43 g (35.6%) of the subject desired compound.

Melting point: 183°–185° C.
IR spectrum $(\lambda_{max}^{KBr})$ cm$^{-1}$: 1780, 1730, 1495.
Mass spectrum (EI/DI) m/z: 268 (M$^+$), 248, 219, 205, 197, 192, 177, 164, 137.

NMR spectrum (DMSO-d$_6$) δ ppm: 1.83–2.43 (2H, m), 3.90–5.47 (3H, m), 6.80–7.43 (3H, m), 8.50 (1H, br.s), 11.03 (1H, br.s).

REFERENCE EXAMPLE dl-2-Azidomethyl-6-fluoro-2,3-dihydro-spiro[4H-1-benzopyran-4,4'-imidazolidine]-2',5'-dione A mixture of dl-2-chloromethyl-6-fluoro-2,3-dihydro-spiro[4H-1-benzopyran-4,4'-imidazolidine]-2',5'-dione (4.26 g, 15 mmol) obtained through the process as described in Example 7), sodium iodide (600 mg, 4 mmol) and sodium azido (1.47 g, 23 mmol) in 20 ml of N,N-dimethylformamide as heated at reflux temperature for 1.5 hours and then poured onto 50 ml of cracked ice. The resulting precipitate was obtained through a filtration and then partitioned between ethyl acetate and water. The organic layer was washed with water, dried over anhydrous sodium sulfate, filtered and evaporated in vacuo to give a solid. The solid was chromatographed on silica gel, eluted with ethyl acetate to give 3.06 g (70.1%) of the subject desired compound.

Mass spectrum (EI/DI) m/z: 291 (M$^+$), 248, 192.
NMR spectrum (DMSO-d$_6$) δ ppm: 2.00–2.40 (2H, m), 3.56–3.93 (2H, m), 4.83–5.26 (1H, m), 6.86–7.50 (3H, m), 8.48 (1H, br.s), 11.07 (1H, br.s).

EXAMPLE 14 dl-2-Aminomethyl-6-fluoro-2,3-dihydro-spiro[4H-1-benzopyran-4,4'-imidazolidine]-2',5'-dione To a suspension of 20% Pd-C (0.6 g) in 20 ml of 50% aqueous ethanol, a solution of dl-2-azidomethyl-6-fluoro-2,3-dihydro-spiro[4H-1-benzopyran-4,4'-imidazolidine]-2',5'-dione (3.0 g, 10 mmol) (obtained through the process as described in the Reference Example) in 160 ml of ethanol was added at room temperature. The mixture was hydrogenated for 16 hours at room temperature under atmospheric pressure. After filtration, the filtrate was evaporated in vacuo to give a solid. The solid was recrystallized from ethanol to give 2.5 g (84.0%) of the subject desired compound.

Melting point: 231°–233° C. (dec.).
IR spectrum $(\nu_{max}^{KBr})$ cm$^{-1}$: 1775, 1725.
Mass spectrum (EI/DI) m/z: 265 (M$^+$), 248.
NMR spectrum (DMSO-d$_6$) δ ppm: 1.67–2.67 (2H, m), 2.80 (2H, d), 4.33–5.00 (1H, m), 4.83–6.00 (1H, br), 6.77–7.43 (3H, m).

EXAMPLE 15 d-6-Fluoro-2,3-dihydro-8-nitro-2',5'-dioxo-spiro[4H-1-benzopyran-4,4'-imidazolidine]-2-carboxamide d-6-Fluoro-2,3-dihydro-2',5'-dioxo-spiro[4H-1-benzopyran-4,4'-imidazolidine]-2-carboxamide (2.00 g, 7.17 mmol) (obtained through the process as described in Example 3-a) was added to 10 ml of fuming nitric acid (specify gravity: 1.52) under stirring below −30° C. The reaction mixture was stirred below −15° C. for 40 minutes and poured onto 30 ml of cracked ice. Resulting crystals deposited out therein were obtained through a filtration and washed with water. The filtrate was further extracted with ethyl acetate and the organic layer was evaporated in vacuo to give an additional amount of crystals.

The crystals were combined together and recrystallized from methanol to give 2.02 g (87.1%) of the subject desired compound.

Melting point: 269°–270° C.

$[\alpha]_D^{20}$: +274° (methanol).

IR spectrum ($\nu_{max}^{KBr}$) cm$^{-1}$: 1780, 1730, 1670, 1535, 1235.

Mass spectrum (EI/DI) m/z: 324 (M+), 237.

NMR spectrum (DMSO-d$_6$) δ ppm: 1.92–2.90 (2H, m), 5.10–5.50 (1H, m), 7.40–8.25 (4H, m), 8.60 (1H, br), 11.25 (1H, br).

Elementary analysis: $C_{12}H_9FN_4O_6$: Cal.: C, 44.45; H, 2.80; N, 17.28. Found: C, 44.54; H, 2.68; N, 17.17.

EXAMPLE 16 d-8-Amino-6-fluoro-2,3-dihydro-2′,5′-dioxo-spiro[4H-1-benzopyran-4,4′-imidazolidine]-4-carboxamide To a solution of d-6-fluoro-2,3-dihydro-8-nitro-2′,5′-dioxo-spiro[4H-1-benzopyran-4,4′-imidazolidine]-2-carboxamide (1.40 g, 4.32 mmol) (obtained through the process as described in Example 15) in 40 ml of methanol, platinum (IV) oxide (140 mg) was added and the mixture was hydrogenated for 20 hours at room temperature under atmospheric pressure.

The catalyst was filtered off and the filtrate was evaporated in vacuo and the residue was recrystallized from the mixture of methanol and water to give 1.15 g (90.6%) of the subject desired compound.

Melting point: 240°–245° C.

$[\alpha]_D^{20}$: +154° (methanol).

IR spectrum ($\nu_{max}^{KBr}$) cm$^{-1}$: 1770, 1735, 1680, 1495.

Mass spectrum (EI/DI) m/z: 294 (M+).

NMR spectrum (DMSO-d$_6$) δ ppm: 1.67–2.80 (2H, m), 4.80–5.17 (1H, m), 5.70 (2H, br), 6.07 (1H, dd), 6.45 (1H, dd), 7.53 (1H, br), 7.95 (1H, br), 8.28 (1H, br), 10.98 (1H, br).

EXAMPLE 17 dl-6-Fluoro-2,3-dihydro-8-nitro-2′,5′-dioxo-spiro[4H-1-benzopyran-4,4′-imidazolidine]-2-carboxamide dl-6-Fluoro-2,3-dihydro-2′,5′-dioxo-spiro[4H-1-benzopyran-4,4′-imidazolidine]-2-carboxamide (2.00 g, 7.17 mmol) (obtained through the process as described in Example 2) was added to 6 ml of fuming nitric acid (specify gravity: 1.52) under stirring at −30° C. The reaction mixture was stirred below −15° C. for an hour and poured onto 30 ml of cracked ice. Resulting crystals deposited out therein were obtained through a filtration and washed with water, dried and recrystallized from the mixture of N,N-dimethylformamide and methanol to give 1.98 g (85.3%) of the subject desired compound.

Melting point: above 300° C.

IR spectrum ($\nu_{max}^{KBr}$) cm$^{-1}$: 1780, 1735, 1690, 1530, 1240.

Mass spectrum (EI/DI) m/z: 324 (M+), 237.

NMR spectrum (DMSO-d$_6$) δ ppm: 1.92–2.90 (2H, m), 5.10–5.50 (1H, m), 7.40–8.25 (4H, m), 8.60 (1H, br), 11.25 (1H, br).

EXAMPLE 18 dl-8-Amino-6-fluoro-2,3-dihydro-2′,5′-dioxo-spiro[4H-1-benzopyran-4,4′-imidazolidine]-2-carboxamide To a solution of dl-6-fluoro-2,3-dihydro-8-nitro-2′,5′-dioxo-spiro[4H-1-benzopyran-4,4′-imidazolidine]-2-carboxamide (1.40 g, 4.32 mmol) (obtained through the process as described in Example 17) in 20 ml of N,N-dimethylformamide and 40 ml of methanol, platinum (IV) oxide (140 mg) was added and the mixture was hydrogenated for 20 hours at room temperature under atmospheric pressure.

The catalyst was filtered off and the filtrate was evaporated in vacuo and the residue was recrystallized from the mixture of N,N-dimethylformamide and methanol to give 1.17 g (92.1%) of the subject desired compound.

Melting point: 295°–above 301° C.

IR spectrum ($\nu_{max}^{KBr}$) cm$^{-1}$: 1770, 1725, 1675, 1495.

Mass spectrum (EI/DI) m/z: 294 (M+).

NMR spectrum (DMSO-d$_6$) δ ppm: 1.67–2.80 (2H, m), 4.80–5.17 (1H, m), 5.70 (2H, br), 6.07 (1H, dd), 6.45 (1H, dd), 7.53 (1H, br), 7.95 (1H, br), 8.28 (1H, br), 10.98 (1H, br).

EXAMPLE 19 dl-2-Chloromethyl-6-fluoro-2,3-dihydro-8-nitro-spiro[4H-1-benzopyran-4,4′-imidazolidine]-2′,5′-dione dl-2-Chrolomethyl-6-fluoro-2,3-dihydro-spiro[4H-1-benzopyran-4,4′-imidazolidine]-2′,5′-dione (2.00 g, 7.4 mmol) (obtained through the process as described in Example 7) was added to 6 ml of fuming nitric acid (specify gravity: 1.52) under stirring at −30° C. The reaction mixture was stirred below −15° C. for 1.5 hours and poured onto 30 ml of cracked ice. Resulting crystals deposited out therein were obtained through a filtration, washed with water, dried and recrystallized from methanol to give 1.81 g (78.0%) of the subject desired compound.

Melting point: 210°–213° C.

IR spectrum ($\nu_{max}^{KBr}$) cm$^{-1}$: 1775, 1730, 1540, 1240.

Mass spectrum (EI/DI) m/z: 329 (M+), 293.

NMR spectrum (DMSO-d$_6$) δ ppm: 1.95–2.83 (2H, m), 3.90–4.10 (2H, m), 4.90–5.40 (1H, m), 7.58 (1H, dd), 7.97 (1H, dd), 8.57 (1H, br), 11.23 (1H, br).

EXAMPLE 20 dl-8-Amino-2-chloromethyl-6-fluoro-2,3-dihydro-spiro[4H-1-benzopyran-4,4′-imidazolidine]-2′,5′-dione To a solution of dl-2-chloromethyl-6-fluoro-2,3-dihydro-8-nitro-spiro[4H-1-benzopyran-4,4′-imidazolidine]-2′,5′-dione (1.40 g, 4.26 mmol) (obtained through the process as described in Example 19) in 40 ml of methanol, platinum (IV) oxide (140 mg) was added and the mixture was hydrogenated for 20 hours at room temperature under atmospheric pressure.

After 20 ml of N,N-dimethylformamide was added to the mixture, the catalyst was filtered off and the filtrate was evaporated in vacuo to dryness. The residue was recrystallized from the mixture of N,N-dimethylformamide and methanol to give 1.09 g (85.8%) of the subject desired compound.

Melting point: 260° C.

IR spectrum ($\nu_{max}^{KBr}$) cm$^{-1}$: 3420, 3330, 1775, 1710, 1495.

Mass spectrum (EI/DI) m/z: 299 (M+).

NMR spectrum (DMSO-d$_6$) δ ppm: 1.80–2.65 (2H, m), 3.78–4.10 (2H, m), 4.65–5.35 (3H, m), 6.08 (1H, dd), 6.45 (1H, dd), 8.40 (1H, br), 10.93 (1H, br).

EXAMPLE 21 d-8-Acetamido-6-fluoro-2,3-dihydro-2′,5′-dioxo-spiro[4H-1-benzopyran-4,4′-imidazolidine]-2-carboxamide To a solution of d-8-amino-6-fluoro-2,3-dihydro-2′,5′-dioxo-spiro[4H-1-benzopyran-4,4′-imidazolidine]-2-carboxamide (700 mg, 2.38 mmol) (obtained through the process as described in Example 16) in 15 ml of pyridine, acetyl chloride (190 mg, 2.42 mmol) was added.

The reaction mixture was stirred at room temperature for 4 hours and then evaporated in vacuo to dryness. The residue was chromatographed on silica gel, eluted with chloroform/methanol (5:1) to give crystals. The crystals were recrystallized from methanol to give 615 mg (76.9%) of the subject desired compound.

Melting point: 202°–203° C.
$[\alpha]_D^{20}$: +136° (methanol).
IR spectrum ($\nu_{max}^{KBr}$) cm$^{-1}$: 1780, 1725, 1675, 1540, 1450.
Mass spectrum (EI/DI) m/z: 336 (M$^+$), 277.
NMR spectrum (DMSO-d$_6$) δ ppm: 1.70–2.80 (2H, m), 2.20 (3H, s), 4.93–5.35 (1H, m), 6.78 (1H, dd), 7.73 (1H, br), 7.96 (1H, dd), 8.20 (1H, br), 8.43 (1H, br), 9.55 (1H, br), 11.10 (1H, br).

EXAMPLE 22

(E)-4-(5-Fluoro-2-hydroxyphenyl)-4-oxo-2-butenoic acid

Into 100 ml of 1,2-dichloroethane, maleic anhydride (11.3 g, 114 mmol) and anhydrous aluminum chloride (31.0 g, 228 mmol) were dissolved by heating at 50° C. for 15 minutes, and then p-fluoroanisole (12.6 g, 100 mmol) was added dropwise. The mixture was refluxed for an hour and then poured into 60 ml of concentrated hydrochloric acid with 400 g of cracked ice. Resulting crystals deposited out therein were obtained through a filtration, washed with water and dried in vacuo to give 16.0 g (80.0%) of the subject desired compound as yellow crystals.

Melting point: 189°–191° C.
IR spectrum ($\nu_{max}^{KBr}$) cm$^{-1}$: 1733, 1648.
NMR spectrum (DMSO-d$_6$) δ ppm: 6.70 (1H, d, J=16.0 Hz), 6.7–8.0 (3H, m), 8.00 (1H, d, J=16.0 Hz).

EXAMPLE 23

6-Fluoro-3,4-dihydro-4-oxo-2H-1-benzopyran-2-carboxylic acid

Sodium bicarbonate (2.10 g, 25.0 mmol) was added to a suspension of (E)-4-(5-fluoro-2-hydroxyphenyl)-4-oxo-2-butenoic acid (5.00 g, 23.8 mmol) (obtained through the process as described in Example 22) in 200 ml of distilled water and the mixture was refluxed for 10 minutes. After cooling, the reaction mixture was acidified to pH 1.0 with concentrated hydrochloric acid and then extracted with ethyl acetate. The organic layer was dried over anhydrous sodium sulfate and evaporated in vacuo to give crude crystals which were recrystallized from the mixture of water and methanol to give 4.60 g (92.1%) of the subject desired compound as colorless crystals.

Melting point: 163°–164° C.
IR spectrum ($\nu_{max}^{KBr}$) cm$^{-1}$: 1755, 1650.
Mass spectrum (EI/DI) m/z: 210 (M$^+$), 165.
NMR spectrum (DMSO-d$_6$) δ ppm: 3.08 (1H, d, J=8.0 Hz), 3.10 (1H, d, J=6.0 Hz), 5.33 (1H, dd, J=8.0 and 6.0 Hz), 7.1–7.8 (3H, m).

EXAMPLE 24 d- and 1-N-[(S)-1-Methylbenzyl]-6-fluoro-3,4-dihydro-4-oxo-2H-1-benzopyran-2-carboxamide Thionylchloride (71.5 g), 0.600 mol) was added to the solution of dl-6-fluoro-3,4-dihydro-4-oxo-2H-1-benzopyran-2-carboxylic acid (84.0 g, 0.400 mol) (obtained through the process as described in Example 23) in 840 ml of 1,2-dichloroethane. After refluxed for an hour, the reaction mixture was evaporated in vacuo to give crystals (91.0 g) of 6-fluoro-3,4-dihydro-4-oxo-2H-1-benzopyran-2-carbonyl chloride. The crystals were dissolved in 50 ml of dichloromethane and resulting solution was added dropwise at 0° to 5° C. into a solution of (S)-(−)-1-methylbenzylamine (48.4 g, 0.400 mol) and triethylamine (40.5 g, 0.400 mol) in 800 ml of dichloromethane.

The mixture was stirred for an hour and then partitioned with water. Dichloromethane layer was separated, dried over anhydrous sodium sulfate and evaporated in vacuo to give crystals (124 g, 99.0%) of diastereomer mixture of N-[(S)-1-methylbenzyl]-6-fluoro-3,4-dihydro-4-oxo-2H-1-benzopyran-2-carboxamide.

The diostereomer mixture was recrystallized from 1 liter of ethanol twice to give 41.8 g (67.5%) of d-N-[(S)-1-methylbenzyl]-6-fluoro-3,4-dihydro-4-oxo-2H-1-benzopyran-2-carboxamide.

Melting point: 170°–172° C.
$[\alpha]_D^{20}$: +5° (methanol).
Mass spectrum (EI/DI) m/z: 313 (M$^+$), 105.
NMR spectrum (CDCl$_3$) δ ppm: 1.48 (3H, d, J=7.0 Hz), 2.7–3.4 (2H, m), 4.8–5.5 (2H, m), 6.8–7.7 (9H, m).

The mother liquor, which was the filtrate after the filtration of the crystalline mass of d-N-[(S)-1-methylbenzyl]-6-fluoro-3,4-dihydro-4-oxo-2H-1-benzopyran-2-carboxamide, was evaporated in vacuo to dryness. The residue was recrystallized from 1 liter of the mixture of ethyl acetate and n-hexane (2:1) twice to give 24.4 g (39.4%) of 1-N-[(S)-1-methylbenzyl]-6-fluoro-3,4-dihydro-4-oxo-2H-1-benzopyran-2-carboxamide.

Melting point: 127°–128° C.
$[\alpha]_D^{20}$: −108° (methanol).
Mass spectrum (EI/DI) m/z: 313 (M$^+$), 105.
NMR spectrum (CDCl$_3$) δ ppm: 1.53 (3H, d, J=7.0 Hz), 2.7–3.4 (2H, m),
4.8–5.5 (2H, m), 6.8–7.7 (9H, m).

EXAMPLE 25 d-6-Fluoro-3,4-dihydro-4-oxo-2H-1-benzopyran-2-carboxylic acid

A mixture of d-N-[(S)-1-methylbenzyl]-6-fluoro-3,4-dihydro-4-oxo-2H-1-benzopyran-2-carboxamide (127 g, 0.410 mol) (obtained through the process as described in Example 24), concentrated hydrochloric acid (600 ml) and 1,4-dioxane (800 ml) was refluxed for 2 hours. After cooling, the reaction mixture was extracted twice with dichloromethane.

The organic layer was dried over anhydrous sodium sulfate and evaporated in vacuo to give 72.9% (85.5%) of the subject desired compound as colorless crystals.

Melting point: 175°–177° C.
$[\alpha]_D^{20}$ +58° (methanol).
Mass spectrum (EI/DI) m/z: 210 (M$^+$), 165.
H-NMR spectrum (DMSO-d$_6$) δ ppm: 3.08 (1H, d, J=8.0 Hz), 3.10 (1H, d, J=6.0 Hz), 5.33 (1H, dd, J=8.0 and 6.0 Hz), 7.1–7.8 (3H, m).
Elementary analysis: C$_{10}$H$_7$FO$_4$: Cal.: C, 57.15; H, 3.36. Found: C, 57.10; H, 3.29.

EXAMPLE 26

1-6-Fluoro-3,4-dihydro-4-oxo-2H-1-benzopyran-2-carboxylic acid

The operation as described in Example 25 was repeated except that 1-N-[(S)-1-methylbenzyl]-6-fluoro-3,4-dihydro-4-oxo-2H-1-benzopyran-2-carboxamide (110 g, 0.350 mol) (obtained through the process as described in Example 24) was employed as the starting material in lieu of the corresponding d-type compound. In this case, 68.2 g (92.4%) of the subject desired compound were obtained.

Melting point: 173°-175° C.
$[\alpha]_D^{20}$: −56° (methanol).
Mass spectrum (EI/DI) m/z: 210 (M+), 165.
H-NMR spectrum (DMSO-d$_6$) δ ppm: 3.08 (1H, d, J=8.0 Hz), 3.10 (1H, J=6.0 Hz), 5.33 (1H, dd, J=8.0 and 6.0 Hz), 7.1-7.8 (3H, m).

EXAMPLE 27 d-6-Fluoro-2,3-dihydro-2',5'-dioxo-spiro[4H-1-benzopyran-4,4'-imidazolidine]-2-carboxylic acid The operation as described in Example 1 was repeated except that d-6-fluoro-3,4-dihydro-4-oxo-2H-1-benzopyran-2-carboxylic acid (54.8 g, 0.216 mol) (obtained through the process as described in Example 25) was employed as the starting material in lieu of the corresponding dl-type compound. In this case, 35.5 g (48.6%) of the subject desired compound were obtained.

Melting point: 146° C.
$[\alpha]_D^{27}$: +194° (methanol).
IR spectrum ($\nu_{max}^{KBr}$) cm$^{-1}$: 3336, 1787, 1735, 1718.
Mass spectrum (EI/DI) m/z: 280 (M+), 262, 164.

EXAMPLE 28

1-6-Fluoro-2,3-dihydro-2',5'-dioxo-spiro[4H-1-benzopyran-4,4'-imidazolidine]-2-carboxylic acid The operation as described in Example 1 was repeated except that 1-6-fluoro-3,4-dihydro-4-oxo-2H-1-benzopyran-2-carboxylic acid (250 g, 1.19 mol) (obtained through the process as described in Example 26) was employed as the starting material in lieu of the corresponding dl-type compound. In this case, 202 g (48.6%) of the subject desired compound were obtained.

Melting point : 145° C.
$[\alpha]_D^{27}$: −193° (methanol).
IR spectrum ($\nu_{max}^{KBr}$) cm$^{-1}$: 3338, 1787, 1735, 1716.
Mass spectrum (EI/DI) m/z : 280 (M+), 262, 164.

EXAMPLE 29 d-6-Fluoro-2,3-dihydro-2',5'-dioxo-spiro[4H-1-benzopyran-4,4'-imidazolidine]-2-carboxylic acid n-propyl ester A mixture of d-6-Fluoro-2,3-dihydro-2',5'-dioxo-spiro[4H-1-benzopyran-4,4'-imidazolidine]-2-carboxylic acid (5.0 g, 0.018 mol) (obtained through the process as described in Example 27), concentrated sulfuric acid (0.125 ml, 2.35 mmol), benzene (5 ml, 0.056 mol) and n-propyl alcohol (20 ml, 0.268 mol) was refluxed for 5.0 hours, while azeotropically removing water by setting a Dean-Stark trap. The reaction mixture was concentrated to half volume and partitioned between 100 ml of ethyl acetate and 50 ml of 5% aqueous solution of sodium bicarbonate. The organic layer was separated from the aqueous layer, dried over anhydrous sodium sulfate and evaporated in vacuo to dryness. To the residue, 50 ml of water were added and then the aqueous solution was stirred for an hour. Resulting crystals deposited out therein were obtained through a filtration and dried to give 5.60 g (97.1%) of the subject desired compound.

Melting point : 197°-200° C.
$[\alpha]_D^{26}$: +165° (methanol).
IR spectrum ($\nu_{max}^{KBr}$) cm$^{-1}$: 3340, 3265, 1788, 1750, 1720.
Mass spectrum (EI/DI) m/z : 322 (M+), 192.
Elementary analysis : C$_{15}$H$_{15}$FN$_2$O$_5$: Cal. : C, 55.90; H, 4.69; N, 8.69. Found : C, 55.91; H, 4.66; N, 8.88.

EXAMPLE 30

1-6-Fluoro-2,3-dihydro-2',5'-dioxo-spiro[4H-1-benzopyran-4,4'-imidazolidine]-2-carboxylic acid n-propyl ester The operation as described in Example 29 was repeated except that 1-6-fluoro-3,4-dihydro-2',5'-dioxo-spiro[4H-1-benzopyran-4,4'-imidazolidine]-2-carboxylic acid (5.0 g, 18 mmol) (obtained through the process as described in Example 28) was employed as the starting material in lieu of the corresponding d-type compound. In this case, 5.7 g (quantitative) of the subject desired compound were obtained.

$[\alpha]_D^{26}$: −163° (methanol).
Elementary analysis: C$_{15}$H$_{15}$FN$_2$O$_5$: Cal. : C, 55.90; H, 4.69; N, 8.69. Found : C, 55.98; H, 4.79; N, 8.67.

EXAMPLE 31 dl-6-Fluoro-2,3-dihydro-2',5'-dioxo-spiro[4H-1-benzopyran-4,4'-imidazolidine]-2-carboxylic acid n-propyl ester The operation as described in Example 29 was repeated except that dl-6-fluoro-3,4-dihydro-2',5'-dioxo-spiro[4H-1-benzopyran-4,4'-imidazolidine]-2-carboxylic acid (5.0 g, 18 mmol) (obtained through the process as described in Example 1) was employed as the starting material in lie of the corresponding d-body compound. In this case, 5.7 g (quantitative) of the subject desired compound were obtained.

Mass spectrum (EI/DI) m/z : 322 (M+), 192.
NMR spectrum (DMSO-d$_6$) δ ppm : 0.92 (3H, t), 1.68 (2H, hexlet), 2.00-2.90 (2H, m), 4.20 (2H, t), 5.38 (1H, dd), 6.90-7.50 (3H, m), 8.48 (1H, br.s), 11.10 (1H, br.s).
Elementary analysis : C$_{15}$H$_{15}$FN$_2$O$_5$: Cal. : C, 55.90; H, 4.69; N, 8.69. Found : C, 55.93; H, 4.65; N, 8.87.

EXAMPLE 32

[d-6-Fluoro-2,3-dihydro-2',5'-dioxo-spiro[4H-1-benzopyran-4,4'-imidazolidine]-2-carboxylic acid methyl ester The operation as described in Example 4 was repeated except that d-6-fluoro-3,4-dihydro-2',5'-dioxo-spiro[4H-1-benzopyran-4,4'-imidazolidine]-2-carboxylic acid (35.0 g, 0.125 mol) (obtained through the process as described in Example 27) was employed as the starting material in lieu of the corresponding dl-type compound. In this case, 33.6 g (91.6%) of the subject compound were obtained.

Melting point : 340° C.
$[\alpha]_D^{20}$: +186° (N,N-dimethylformamide).
IR spectrum ($\nu_{max}^{KBr}$) cm$^{-1}$: 3350, 3280, 1790, 1740.
Mass spectrum (EI/DI) m/z : 294 (M+), 262.
NMR spectrum (DMSO-d$_6$) δ ppm : 1.92-2.85 (2H, m), 3.81 (3H, s), 5.40 (1H, dd), 6.90-7.40 (3H, m), 8.50 (1H, br), 11.12 (1H, br).

EXAMPLE 33 d-6-Fluoro-2,3-dihydro-2',5'-dioxo-spiro[4H-1-benzopyran-4,4'-imidazolidine]-2-carboxamide (a) To a suspension of d-6-fluoro-2,3-dihydro-2',5'-dioxo-spiro[4H-1-benzopyran-4,4'-imidazolidine]-2-carboxylic acid n-propyl ester (1.00 g, 3.11 mmol) (obtained through the process as described in Example 29) in 5.0 ml of methanol, an excess amount of dry ammonia gas was perfused below 24° C. The mixture was stirred for 4.0 hours at 20°–24° C. and then evaporated in vacuo to dryness. To the residue, 10 ml of water were added. After stirring for an hour, the aqueous solution was acidified with 6N-hydrochloric acid solution. Resulting crystals were obtained through a filtration and dried to give 800 mg (90%) of the subject desired compound which had same physical properties with those of the crystals obtained in Example 3-a.

(b) The operation as described in said Item a was repeated except that d-6-fluoro-2,3-dihydro-2′,5′-dioxo-spiro[4H-1-benzopyran-4,4′-imidazolidine]-2-carboxylic acid methyl ester (30.0 g, 0.102 mol) (obtained through the process as described in Example 32) was emploed as the starting material in lieu of the n-propyl ester. In this case, 20.7 g (72.6%) of the subject desired compound were obtained as crystals which had same physical properties with those of the crystals obtained in Example 3-a.

EXAMPLE 34

1-6-Fluoro-2,3-dihydro-2′,5′-dioxo-spiro[4H-1-benzopyran-4,4′-imidazolidine]-2-carboxamide The operation as described in Example 33-a was repeated except that 1-6-fluoro-2,3-dihydro-2′,5′-dioxo-spiro[4H-1-benzopyran-4,4′-imidazolidine]-2-carboxylic acid n-propyl ester (5.75 g, 18 mmol) (obtained through the process as described in Example 30) was employed as the starting material in lieu of the corresponding d-type compound. In this case, 4.9 g (quantitative) of the subject desired compound were obtained [as crystals which had same physical properties with those of the crystals obtained in Example 3-b].

EXAMPLE 35 d-6-Fluoro-2,3-dihydro-2-hydroxymethyl-spiro[4H-1-benzopyran-4,4′-imidazolidine]-2′,5′-dione To a suspension of lithium aluminum hydride (57 mg, 1.5 mmol) in 2.5 ml of tetrahydrofuran, a solution of d-6-fluoro-2,3-dihydro-2′,5′-dioxo-spiro[4H-1-benzopyran-4,4′-imidazolidine]-2-carboxylic acid n-propyl ester (322 mg, 1.0 mmol) (obtained through the process as described in Example 29) in 2.2 ml of tetrahydrofuran was added at 5° C.

After stirring the mixture for 20 hours at room temperature (15°–20° C.), the reaction mixture was poured onto 4.0 ml of cracked ice under stirring. While cooling the solution at room temperature, the solution was acidified to pH 1 by adding concentrated hydrochloric acid and extracted with ethyl acetate.

The organic layer was washed with water, dried over anhydrous sodium sulfate, filtered and evaporated in vacuo to give a solid. The solid was recrystallized from methanol to give 246 mg (92.5%) of the desired compound.

Melting point : 188°–189° C.

$[\alpha]^{20}$ : +222° (methanol).

Elementary analysis : $C_{12}H_{11}FN_2O_4$: Cal. : C, 51.14; H, 4.16; N, 10.52. Found: C, 54.29; H, 4.25; N, 10.53.

EXAMPLE 36

1-6-Fluoro-2,3-dihydro-2-hydroxymethyl-spiro[4H-1-benzopyran-4,4′-imidazolidine]-2′,5′-dione The operation as described in Example 35 was carried except that 1.-6-fluoro-2,3-dihydro-2′,5′-dioxo-spiro[4H-1-benzopyran-4,4′-imidazolidine]-2-carboxylic acid n-propyl ester (322 mg, 1.0 mmol) (obtained through the process as described in Example 30) was employed as the starting material in lieu of the corresponding d-isomer. In this case, 247 mg (92.9%) of the desired compound was obtained.

Melting point : 188°–189° C.

$[\alpha]^{20}$ : −231° (methanol).

Elementary analysis: $C_{12}H_{11}FN_2O_4$: Cal. : C, 51.14; H, 4.16; N, 10.52. Found: C, 54.31; H, 4.15; N, 10.54.

The invention will now be further explained with reference to Pharmacological Test Examples, and please note that Test Compounds and Control Compounds referred to in such Examples are as follows.

TEST COMPOUNDS

A : dl-6-Fluoro-2,3-dihydro-2′,5′-dioxo-spiro[4H-1-benzopyran-4,4′-imidazolidine]-2-carboxamide (Example 2), B : d-6-Fluoro-2,3-dihydro-2′,5′-dioxo-spiro[4H-1-benzopyran-4,4′-imidazolidine]-2-carboxamide (Examples 3-a and 33)

C : 1-6-Fluoro-2,3-dihydro-2′,5′-dioxo-spiro[4H-1-benzopryan-4,4′-imidazolidine]-2-carboxamide (Examples 3-b and 34), D : d2-2-Chloromethyl-6-fluoro-2,3-dihydro-spiro[4H-1-benzopyran-4,4′-imidazolidine]-2′,5′-dione (Example 7), E : d-2-Chloromethyl-6-fluoro-2,3-dihydro-spiro[4H-1-benzopyran-4,4′-imidazolidine]-2′,5′-dione (Example 8), F : 1-2-Chloromethyl-6-fluoro-2,3-dihydro-spiro[4H-1-benzopyran-4,4′-imidazolidine]-2′,5′-dione (Example 9), G : dl-2-Bromomethyl-6-fluoro-2,3-dihydro-spiro[4H-1-benzopyran-4,4′-imidazolidine]-2′,5′-dione (Example 10), H : d-2-Bromomethyl-6-fluoro-2,3-dihydro-spiro[4H-1-benzopyran-4,4′-imidazolidine]-2′,5′-dione (Example 11), I : 1-2-Bromomethyl-6-fluoro-2,3-dihydro-spiro[4H-1-benzopyran-4,4′-imidazolidine]-2′,5′i-dione (Example 12), J : d-6-Fluoro-2,3-dihydro-8-nitro-2′,5′-dioxo-spiro[4H-1-benzopyran-4,4′-imidazolidine]-2-carboxamide (Example 15), K : d-8-Amino-6-fluoro-2,3-dihydro-2′,5′-dioxo-spiro[4H-1-benzopyran-4,4′-imidazolidine]-2-carboxamide (Example 16), L : dl-6-Fluoro-2,3-dihydro-8-nitro-2′,5′-dioxo-spiro[4H-1-benzopyran-4,4′-imidazolidine]-2-carboxamide (Example 17), M : dl-8-Amino-6-fluoro-2,3-dihydro-2′,5′-dioxo-spiro[4H-1-benzopyran-4,4′-imidazolidine]-2-carboxamide (Example 18), N : dl-2-Chloromethyl-6-fluoro-2,3-dihydro-8-nitro-spiro[4H-1-benzopyran-4,4′-imidazolidine]-2′,5′-dione (Example 19), O : dl-8-Amino-2-chloromethyl-6-fluoro-2,3-dihydro-spiro[4H-1-benzopyran-4,4′-imidazolidine]-2′,5′-dione (Example 20), P : d-8-Acetamido-6-fluoro-2,3-dihydro-2',5'-dioxospiro[4H-1-benzopyran-4,4'-imidazolidine]-2-carboxyamide (Example 21).

effective dose. The selected control compounds are typical one described in the aforesaid Japanese Unexamined Patent Application Gazette.

TABLE 1

| Compound | Inhibition (%) | | | | | | | $IC_{50}$ (M) |
|---|---|---|---|---|---|---|---|---|
| | $10^{-8}$ M | $3.3 \times 10^{-8}$ M | $10^{-7}$ M | $3.3 \times 10^{-7}$ M | $10^{-6}$ M | $3.3 \times 10^{-6}$ M | $10^{-5}$ M | |
| Testing compound | | | | | | | | |
| A | 21 | 51 | 80 | 93 | — | — | — | $3.2 \times 10^{-8}$ |
| B | 39 | 80 | 93 | — | — | — | — | $1.4 \times 10^{-8}$ |
| C | — | — | — | — | — | — | 27 | — |
| D | — | 28 | 53 | 78 | — | — | — | $9.0 \times 10^{-8}$ |
| E | 21 | 38 | 66 | — | — | — | — | $4.7 \times 10^{-8}$ |
| F | — | — | — | — | 28 | 52 | 74 | $2.9 \times 10^{-6}$ |
| G | — | 22 | 42 | 70 | — | — | — | $1.3 \times 10^{-7}$ |
| H | — | 35 | 59 | 82 | — | — | — | $6.8 \times 10^{-8}$ |
| I | — | — | — | — | 31 | 54 | 75 | $2.7 \times 10^{-6}$ |
| Control compound | | | | | | | | |
| Q | — | 10 | 17 | 46 | 71 | 85 | — | $3.9 \times 10^{-7}$ |
| R | — | 15 | 34 | 61 | 80 | 88 | — | $2.0 \times 10^{-7}$ |
| S | — | — | — | — | — | — | 32 | — |

TABLE 2

| Compound | Inhibition (%) | | | | | | $IC_{50}$ (M) |
|---|---|---|---|---|---|---|---|
| | $10^{-8}$ M | $2.0 \times 10^{-8}$ M | $3.3 \times 10^{-8}$ M | $10^{-7}$ M | $3.3 \times 10^{-7}$ M | $10^{-6}$ M | |
| Testing compound | | | | | | | |
| J | 35 | 69 | 82 | — | — | — | $1.4 \times 10^{-8}$ |
| K | 27 | — | 60 | 70 | — | — | $2.5 \times 10^{-8}$ |
| L | 15 | — | 50 | 88 | — | — | $3.1 \times 10^{-8}$ |
| M | 13 | — | 40 | 74 | — | — | $4.4 \times 10^{-8}$ |
| N | — | — | 30 | 59 | 81 | — | $7.6 \times 10^{-8}$ |
| O | — | — | — | 38 | 68 | 85 | $1.7 \times 10^{-7}$ |
| P | 30 | 56 | 69 | — | — | — | $1.8 \times 10^{-8}$ |
| Control compound | | | | | | | |
| R | — | — | 24 | 29 | 59 | 76 | $2.6 \times 10^{-7}$ |

CONTROL COMPOUNDS

Q : dl-6-Fluoro-2,3-dihydro-spiro[4H-1-benzopyran-4,4'-imidazolidine]-2',5'-dione, R : d-6-Fluoro-2,3-dihydro-spiro[4H-1-benzopyran-4,4'-imidazolidine]-2',5'-dione, S : 1-6-Fluoro-2,3-dihydro-spiro[4H-1-benzopyran-4,4'-imidazolidine]-2',5'-dione.

PHARMACOLOGICAL TEST EXAMPLE 1

The compounds according to the invention were tested for their ability to reduce or inhibit aldose reductase enzyme activity, in accordance with the method of Kador and Sharpless as described in "Biophysical Chemistry" Vol. 8, page 81 (1978) and using water soluble extracts of rat lenses. Results are given in following Tables 1 and 2 in terms of percent inhibition of enzyme activity with respect to the various concentrations of $10^{-6}$ —$10^{-8}$ M. The selected control compounds are typical one disclosed in Jap. Unexamined Pat. Appln. Gazette No. 53653/1978 introduced in the preamble of this specification. $IC_{50}$ represents the concentration of inhibitor which gives 50% inhibition.

PHARMACOLOGICAL TEST EXAMPLE 2

The compounds according to the invention were tested for their ability to reduce or inhibit polyol increase in the sciatic nerve of galactosemic rats. Rats were fed 30% galactose diet and were administered the compounds at the various doses of 0.4–50 mg/kg once a day for eight days. One day after the final administration (on 9th day), sciatic nerves were removed for galactitol determination. Results are given in following Tables 3 and 4 in terms of $ED_{50}$ which represents 50%

TABLE 3

| Compound | $ED_{50}$ (mg/kg) |
|---|---|
| Testing compound | |
| A | 3.3 |
| B | 1.3 |
| Control compound | |
| Q | 36.6 |
| R | 18.0 |

TABLE 4

| Compound | $ED_{50}$ (mg/kg) |
|---|---|
| Testing compound | |
| D | 1.3 |
| E | 0.6 |
| G | 7.2 |
| H | 2.2 |
| Control compound | |
| Q | 31.5 |

As apparently seen from the results given in the Tables, the compounds according to the invention give fairly high reduction or inhibition of aldose reductase. Moreover, d and dl-type products according to the invention show superior effect and more particularly d-type product shows extremely high effect on reduction or inhibition of aldose reductase.

PHARMACEUTICAL AGENT PREPARATION EXAMPLE 1 (TABLETS)

Tablets for oral administration, each contains 50 mg of an active ingredient were prepared with following prescription and a method known per se.

| | |
|---|---|
| d-6-Fluoro-2,3-dihydro-2',5'-dioxo-spiro[4H-1-benzopyran-4,4'-imidazolidine]-2-carboxamide (Product of Example 3-a) | 50 (g) |
| Sodium citrate | 25 |
| Alginic acid | 10 |
| Polyvinylpyrrolidone | 10 |
| Magnesium stearate | 5 |

Tablets, each of which contains the active ingredient of 1.0, 4.0, 5.0, 10, 25 and 100 mg, were prepared by varying the mixing amount thereof.

PHARMACEUTICAL AGENT PREPARATION EXAMPLE 2 (CAPSULES)

Capsules for oral administration, each contains 10 mg of an active ingredient were prepared with following prescription and a method known per se.

| | |
|---|---|
| d-2-Chloromethyl-6-fluoro-2,3-dihydro-spiro[4H-1-benzopyran-4,4'-imidazolidine]-2',5'-dione (Product of Example 8) | 10 (g) |
| Lactose | 70 |
| Corn starch | 20 |

What is claimed is:

1. A process for the preparation of an optically active hydantoin derivative of the formula

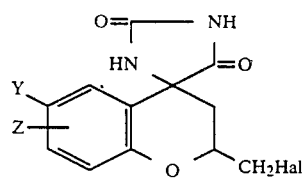

wherein Y and Z are the same or different, each being a hydrogen atom, a halogen atom or an alkyl group having 1 to 4 carbon atoms, and Hal is a halogen atom, which comprises steps of reacting an optically active compound of the formula

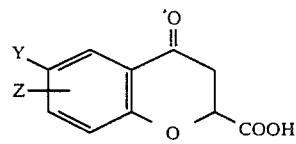

with an alkali metal cyanide and ammonium carbonate, reacting the resulting optically active compound of the formula

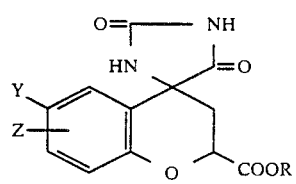

in the presence of a solvent and an acid catalyst, with a compound of the formula ROH, wherein R is an alkyl group having 1 to 4 carbon atoms, while azeotropically removing water as it is formed, reducing the resulting optically active compound of the formula

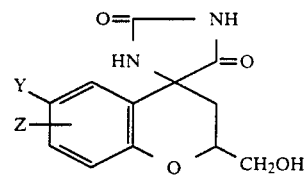

and reacting the alcohol group in the resulting optically active compound of the formula with a halogenating agent.

2. A process as claimed in claim 1, wherein said reduction of the compound IV is carried out using lithium aluminum hydride.

3. A process as claimed in claim 1, wherein said halogenation of the compound V is carried out using thionyl chloride as the halogenating agent.

* * * * *

UNITED STATES PATENT AND TRADEMARK OFFICE
CERTIFICATE OF CORRECTION

PATENT NO. : 5,001,240

DATED : March 19, 1991

INVENTOR(S) : Masayasu Kurono et al

It is certified that error appears in the above-identified patent and that said Letters Patent is hereby corrected as shown below:

On the cover page, Item [75] should add the names of these inventors --Ryoichi UNNO, Hiroshi OZAWA and Masato FUKUSHIMA--.

On the cover page, Item [73] "Sanwa Kagaku Kenkyyusho Co., Ltd." should read --Sanwa Kagaku Kenkyusho Co., Ltd.--.

Signed and Sealed this

Twenty-ninth Day of September, 1992

Attest:

DOUGLAS B. COMER

*Attesting Officer*         *Acting Commissioner of Patents and Trademarks*